United States Patent
Chung et al.

(10) Patent No.: US 9,850,226 B2
(45) Date of Patent: Dec. 26, 2017

(54) LITHIUM-SELECTIVE CROWN ETHER, LITHIUM ADSORBENT USING SAME, AND PREPARATION METHOD THEREOF

(71) Applicant: MYONGJI UNIVERSITY INDUSTRY AND ACADEMIA COOPERATION FOUNDATION, Yongin-si, Gyeonggi-do (KR)

(72) Inventors: Wook-Jin Chung, Seongnam-si (KR); Lawrence A. Limjuco, Yongin-si (KR); Grace M. Nisola, Yongin-si (KR); Rey Eliseo C. Torrejos, Yongin-si (KR); Eleazer L. Vivas, Yongin-si (KR); Hern Kim, Seongnam-si (KR); Myoung Jun Park, Yongin-si (KR); Jeong Gil Seo, Yongin-si (KR); Seong-Poong Lee, Anyang-si (KR)

(73) Assignee: MYONGJI UNIVERSITY INDUSTRY AND ACADEMIA COOPERTAION FOUNDATION, Yongin-si (KR)

( * ) Notice: Subject to any disclaimer, the term of this patent is extended or adjusted under 35 U.S.C. 154(b) by 6 days.

(21) Appl. No.: 14/700,595

(22) Filed: Apr. 30, 2015

(65) Prior Publication Data

US 2016/0280678 A1 Sep. 29, 2016

(30) Foreign Application Priority Data

Mar. 27, 2015 (KR) .................. 10-2015-0043445
Apr. 23, 2015 (KR) .................. 10-2015-0057242

(51) Int. Cl.
| | | |
|---|---|---|
| C07D 323/00 | (2006.01) | |
| B01J 20/26 | (2006.01) | |
| B01J 20/28 | (2006.01) | |
| B01J 20/30 | (2006.01) | |
| D01D 5/00 | (2006.01) | |
| D01F 1/10 | (2006.01) | |
| D01F 11/06 | (2006.01) | |

(52) U.S. Cl.
CPC .......... *C07D 323/00* (2013.01); *B01J 20/267* (2013.01); *B01J 20/28023* (2013.01); *B01J 20/3007* (2013.01); *B01J 20/3042* (2013.01); *D01D 5/003* (2013.01); *D01F 1/10* (2013.01); *D01F 11/06* (2013.01); *D10B 2321/06* (2013.01)

(58) Field of Classification Search
CPC ... C07D 323/00; B01J 20/267; B01J 20/3007; B01J 20/303042; D01F 1/06; D01F 5/003; D01F 1/10; D10B 2321/06
See application file for complete search history.

(56) References Cited

FOREIGN PATENT DOCUMENTS

| JP | 2950430 B2 | 7/1999 |
| KR | 10-2010-0138503 A | 12/2010 |
| KR | 10-2014-0118748 A | 10/2014 |

OTHER PUBLICATIONS

Yu, Zong-Yuan, "Synthesis of Di-areno-14-crown-4-diols and Separation of Their Isomers", Youji Huaxue, vol. 12 Issue: 2, p. 146-150 (1992).*
Olsher et al., "Synthesis and Selectivity of sym-Hydroxydibenzo-14-crown-4 Ionophores for Protons, Alkali Metal Cations, and Alkaline Earth Cations in Polymeric Membranes", Journal of Inclusion Phenomena and Molecular Recognition in Chemistry 9: 125-135, 1990.*
Torrejos et al., "Synthesis and characterization of multi-walled carbon nanotubes-supported dibenzo-14-crown-4 ether with proton ionizable carboxyl sidearm as Li+ adsorbents", Chemical Engineering Journal, vol. 264, pp. 89-98, (2015).
Park et al., "Recyclable composite nanofiber adsorbent for Li+ recovery from seawater desalination retentate", Chemical Engineering Journal, vol. 254, pp. 73-81, (2014).
Yuan et al., Petrochemical Technology, vol. 34(1), pp. 46-50, 2005.
Bartsch et al., "High lithium selectivity in competitive alkali metal solvent extraction by lipophilic crown carboxylic acids", J. Am. Chem. Soc., vol. 107, No. 17, pp. 4997-4998, (1985).
Sachleben et al., "An efficient synthesis of lithium-selective extractants: Tertiary-alkyl-14-crown-4 ethers", Tetrahedron Letters, vol. 34, Issue 34, pp. 5373-5376, (1993).
Sachleben et al., "Conformational changes of substituted 14-crown-4 ethers upon complexation", J. Chem. Soc., Perkin Trans. 2, pp. 1971-1977, (1992).
Torrejos, "Synthesis of 14-Crown-4 Ethers for Lithium Recovery", Dissertation of one of inventors submitted in Feb. 2015 and available online, Graduate School, Myongji University, Department of Energy and Biotechnology, (2015).

* cited by examiner

*Primary Examiner* — Jeffrey Mullis
(74) *Attorney, Agent, or Firm* — Vorys, Sater, Seymour & Pease LLP; Mih Suhn Koh

(57) ABSTRACT

Disclosed herein are a novel crown ether with bulky and rigid groups and a method for preparing the same. Also provided are a lithium adsorbent comprising the novel crown ether immobilized onto a nanofiber, and a method for preparing the same. The lithium-selective crown ether is synthesized through intermolecular cyclization between a bulky epoxide and a rigid aromatic compound such as 1,2-dihydroxybenzene, and can effectively recover lithium ions. For use as a lithium adsorbent, the novel crown ether with both bulky and rigid subunits is immobilized onto a polymer nanofiber. The crown ether-immobilized polymer nanofibers may be formed into a recyclable membrane.

16 Claims, 16 Drawing Sheets
(1 of 16 Drawing Sheet(s) Filed in Color)

LITHIUM-SELECTIVE CROWN ETHER, LITHIUM ADSORBENT USING SAME, AND PREPARATION METHOD THEREOF

BACKGROUND OF THE INVENTION

1. Field of the Invention

The present invention relates to a lithium-selective crown ether, a lithium adsorbent using the same, and a preparation method thereof. More particularly, the present invention relates to a novel crown ether with bulky and rigid groups and a method for preparing the same. Also, the present invention is concerned with a lithium adsorbent comprising the novel crown ether immobilized onto a nanofiber, and a method for preparing the same.

2. Description of the Related Art

Crown ethers are known to strongly bind certain cations, especially alkali metal ions, forming complexes. For example, a 12- to 14-membered crown ether rings have high affinity for lithium ion ($Li^+$), forming complexes with the cation in both oleaginous and aqueous solutions. Dibenzo-14-crown-4 ether (DB14C4) and its derivatives are used as a lithium ion (Li+) complexant because the benzo group provides rigidity and the 14-crown-4 ether backbone has cavity dimensions ideal for complexing with lithium ion. However, because DB14C4 is difficult to synthesize, it has been used as a lithium ion carrier in highly sensitive electrodes or liquid-liquid extraction systems. Many efforts have been made to develop new effective techniques for synthesizing DB14C4, but the products are difficult to prevent from complexing with metal ions larger than lithium ions.

With the problems of conventional techniques in mind, the present inventors conceived a method for synthesizing a lithium-selective crown ether by intermolecular cyclization between a bulky bis-epoxide and a compound containing a rigid aromatic group, such as 1,2-dihydroxybenzene. The crown ether has both rigid and bulky subunits. In the lithium-selective crown ether of the present invention, the aromatic group is responsible for the rigidity of the crown ether backbone while the bulky subunit accounts for the mechanism of blocking complex formation with larger metal ions.

In addition, a $Li^+$ adsorbent comprising the novel crown ether immobilized onto a polymeric support is provided. The polymeric support can be prepared in the form of nanofibers by electrospinning. The nanofibers have a diameter on a micron- to sub-micron scale, with a large surface area per unit volume. For immobilization onto the polymeric ingredient, the crown ether ingredient may be directly added to the polymeric ingredient prior to electrospinning. The crown ether (CE)-polymeric nanofiber prepared by electrospinning can be crosslinked in an aerosol manner using a crosslinker.

RELATED ART DOCUMENT

Bartsch, R. A.; Czech, B. P.; Kang, S. I.; Stewart, L. E.; Wlkowiak, W.; Charewicz, W. A.; Heo, G. S.; Son, B. J. Am. Chem. Soc., 1985, 107, 4997-4998.

Sachleben, R. A,; Davis, M. C.; Bruce, J. J.; Ripple, E. S.; Driver, J. L.; Moyer, B. A. Tetrahedron Lett. 1993, 34, 34, 5373-5376.

Sachleben, R. A.; Burns, J. H. J. Chem. Soc. Perkin Trans. 1992, 1971-1977.

SUMMARY OF THE INVENTION

The present invention provides a novel crown ether having both a bulky subunit and a rigid subunit. Also, the present invention provides a method for preparing a lithium-selective crown ether through intermolecular cyclization between a bulky epoxide and a rigid aromatic compound. Further, the present invention provides a lithium adsorbent comprising a novel crown ether, immobilized onto a polymer support (nanofiber), having both bulky and rigid groups, and a method for preparing the same.

The present invention provides a method for preparing a lithium-selective crown ether, comprising cyclization between a bis-epoxide and a hydroxy benzene.

The bis-epoxide may be synthesized by reacting a diol with an allyl compound to give a di-alkene compound (step a), and then reacting the di-alkene compound with a benzoic acid (step b).

Cyclization

The cyclization may be performed by reacting a bis-epoxide with a hydroxy benzene in the presence of a metal hydroxide in a solvent.

Briefly, the cyclization may be achieved by adding a bis-epoxide to a solution of benzene and a metal hydroxide in a solvent, and stirring the solution for 3 to 9 hrs, and preferably for 6 hrs. After the stirring step, a metal hydroxide may be further added.

In greater detail, to a solution in which a hydroxybenzene and a metal hydroxide are dissolved at a molar ratio of 1:1, a bis-epoxide is added at an equimolar ratio with the hydroxybenzene, followed by stirring. Subsequently, the metal hydroxide is further added in the same amount to the solution, which is then refluxed for 36 to 54 hrs, and more preferably for 42 hrs. The reflux step may be conducted by stirring under reflux.

In one exemplary embodiment, the hydroxybenzene may be 1,2-dihydroxybenzene.

The metal hydroxide may be selected from the group consisting of LiOH, NaOH, KOH, and a combination thereof. The metal hydroxide functions as a catalyst (template ion). A template ion plays an important role in cyclization. Without a template ion having a suitable size for preparing a crown ether of interest, a desired production yield cannot be obtained.

For use in the solution used in the cyclization, a solvent may be selected from the group consisting of t-BuOH, THF, a mixture of THF and $H_2O$, and a combination thereof.

The crown ether may be selected from the group consisting of:

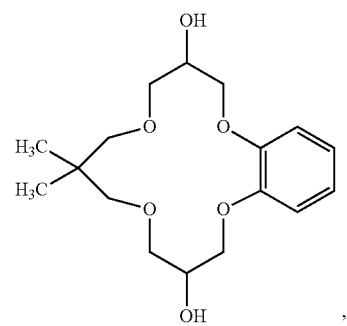

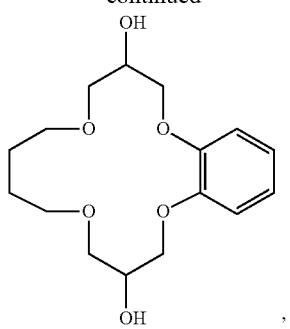

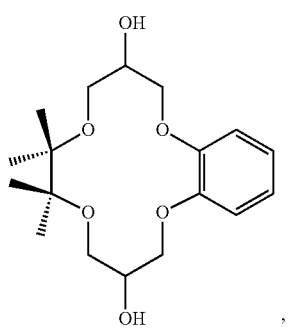

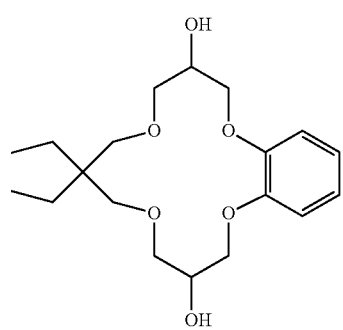

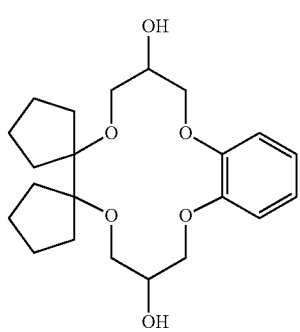

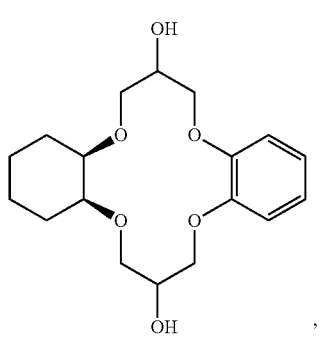

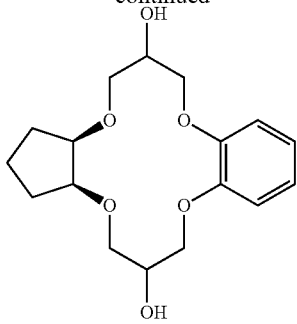

and a combination thereof.

Synthesis of Bis-Epoxide

Synthesis of Di-Alkene Compound

In step a, a diol and an allyl compound are mixed at a molar ratio of 1:2, and the mixture is refluxed for 12 to 48 hrs, and preferably for 24 hrs.

The diol may be selected from the group consisting of pinacol, 2,2-diethyl-1,3-propanediol, [1,1'-bicyclopentyl]-1,1'-diol, cis-1,2-cyclohexanediol, cis-1,2-cyclopentanediol, and a combination thereof.

The allyl compound may be an allyl bromide.

With regard to the di-alkene compound, selection may be made from the group consisting of:

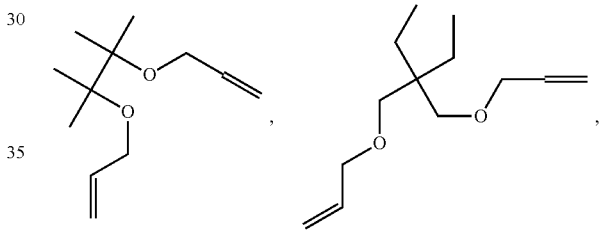

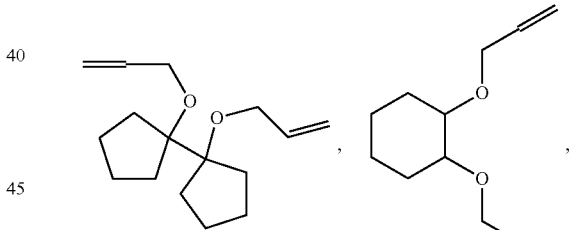

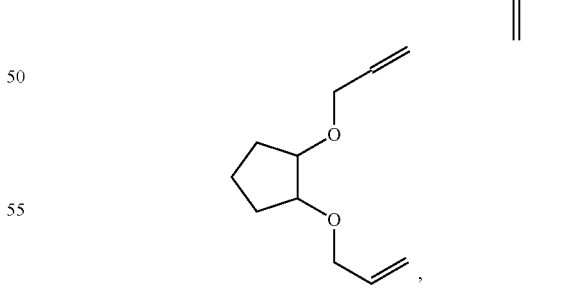

and a combination thereof.

Reaction of Di-Alkene Compound with Benzoic Acid

In step b, the di-alkene compound is mixed at a molar ratio of 1:2.5 with a benzoic acid, followed by stirring the mixture at room temperature for 12 to 36 hrs, and preferably for 24 hrs.

The benzoic acid may be m-chloroperbenzoic acid (m-CPBA).

The bis-epoxide may be selected from the group consisting of:
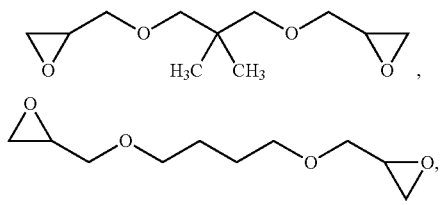
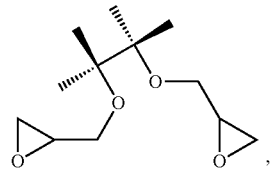
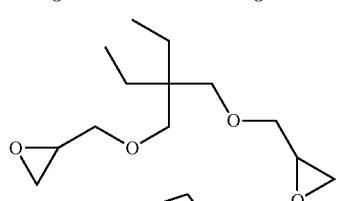
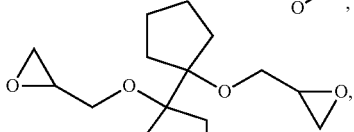
and a combination thereof.
Also contemplated in accordance with another aspect of the present invention is a lithium-selective crown ether comprising a compound selected from the group consisting of:

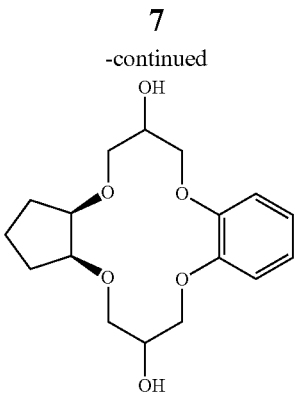

In accordance with a further aspect thereof, the present invention provides a method for preparing a lithium adsorbent based on a crown ether, comprising: mixing the crown ether and a polymeric material in a solvent to give a viscous solution (step a'); electrospinning the viscous solution into polymeric nanofibers (step b'); and crosslinking the nanofibers through a crosslinker to immobilize the crown ether onto the polymeric nanofibers (step c').

The crown ether of step a' may be selected from the group consisting of:

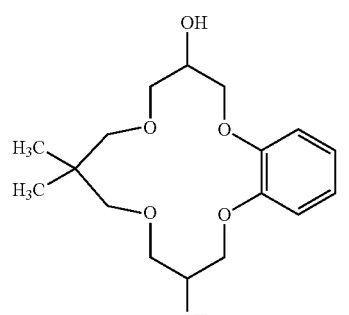

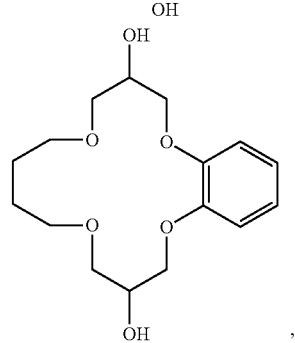

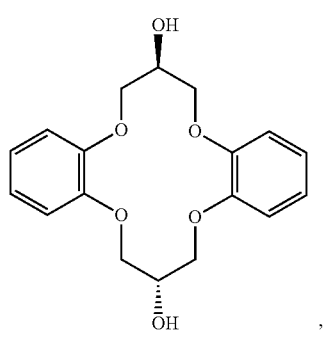

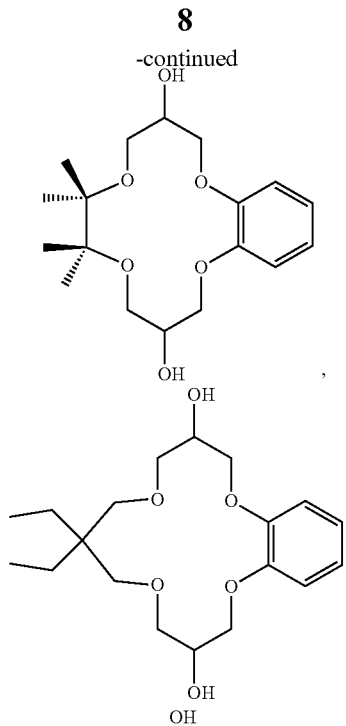

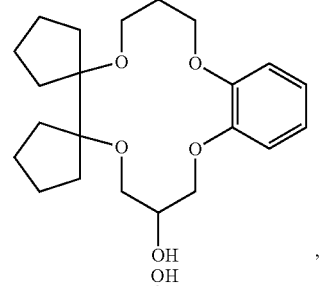

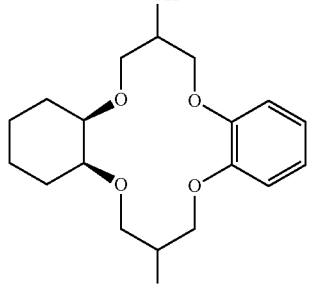

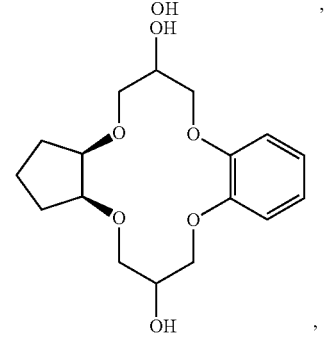

and a combination thereof.

The crown ether used in step a' may be prepared in the same manner as was described above for the preparation method of the lithium-selective crown ether.

The polymer material may be a polyvinyl alcohol (PVA).

The solvent of step a' may be deionized water.

The crosslinking step may be carried out in an aerosol manner.

The crosslinker of step c' may be glutaraldehyde.

In step c', glutaraldehyde may be used as the crosslinker, and glutaraldehyde may be used in the form of an aceton solution prepared by being dissolved in acetone. Based on the total volume of the acetone solution, glutaraldehyde may be contained in an amount of about 10 volume %.

The acetone solution may further contain HCl.

Based on the total volume of the acetone solution, HCl may be contained in an amount of 1 volume °.

The lithium-selective crown ether immobilized onto the polymer nanofiber may be used as a lithium adsorbent.

Accordingly, contemplated in accordance with the present invention is a lithium adsorbent using a crown ether. The crown ether may be immobilized onto a polymer nanofiber, and may be selected from the group consisting of:

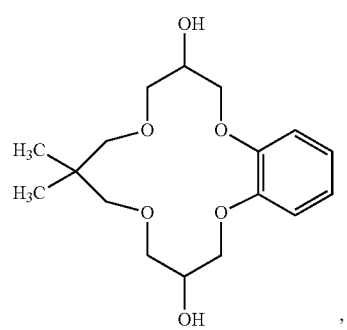

,

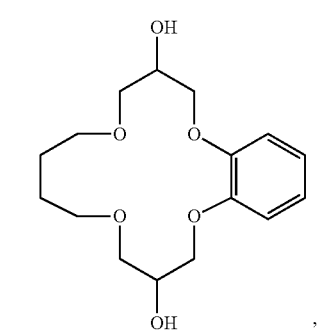

,

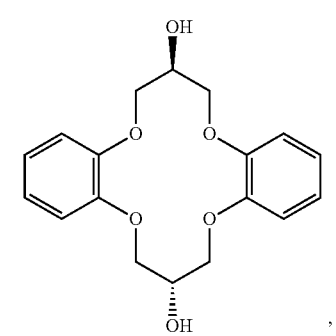

,

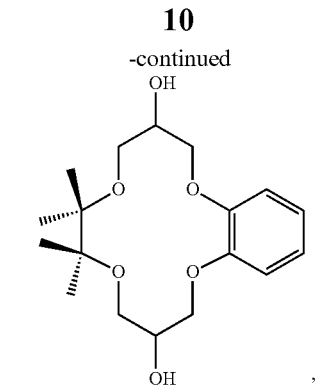

,

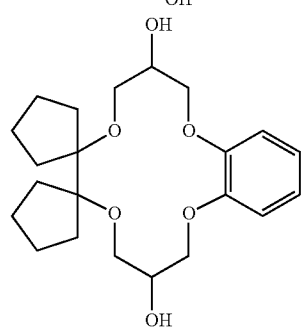

,

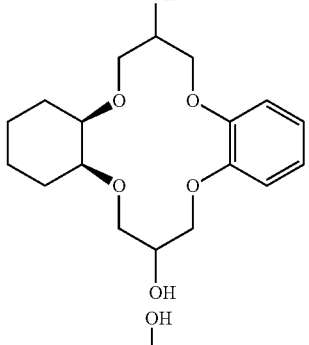

,

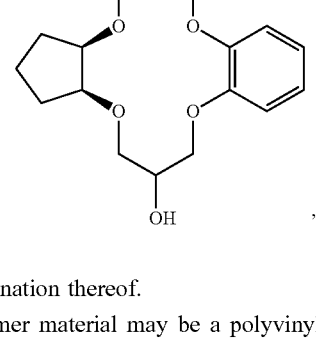

, and a combination thereof.

The polymer material may be a polyvinyl alcohol. The crown ether may be lithium selective.

Moreover, the present invention provides a method for recovering lithium from a lithium source solution, using the lithium adsorbent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will be more clearly understood from the following detailed description taken in conjunction with the accompanying drawings, in which.

DESCRIPTION OF THE PREFERRED EMBODIMENTS

Figure 1:
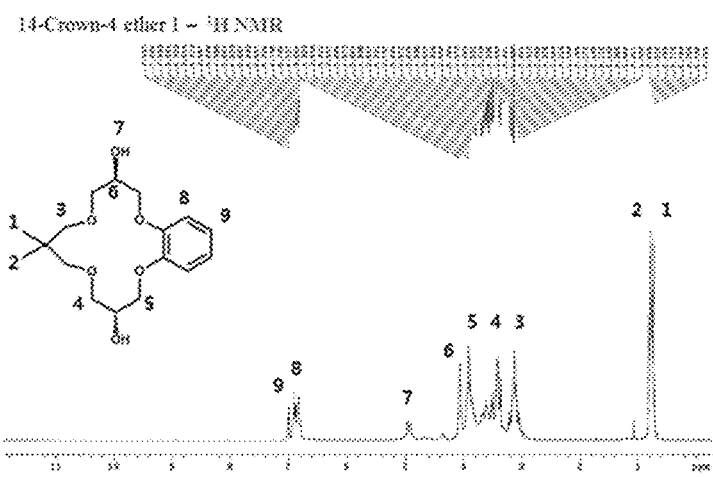
FIGS. 1 to 6 are $^1$H and spectra of 14-crown-4 ethers synthesized according to one exemplary embodiment of the present invention.
Figure 2:
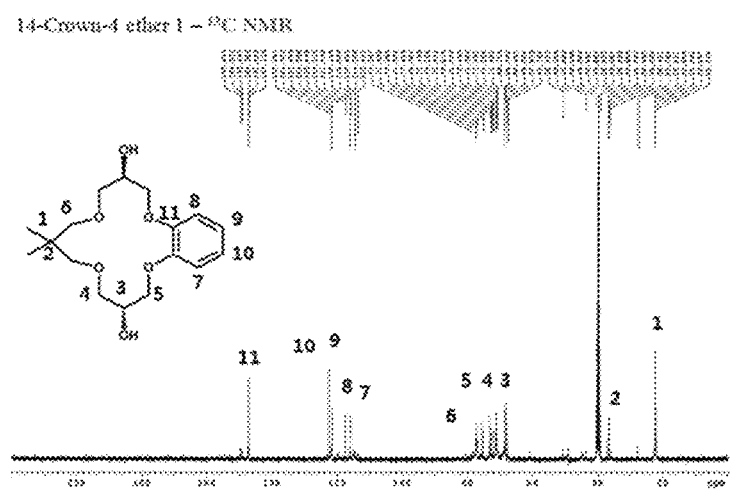
Figure 3:
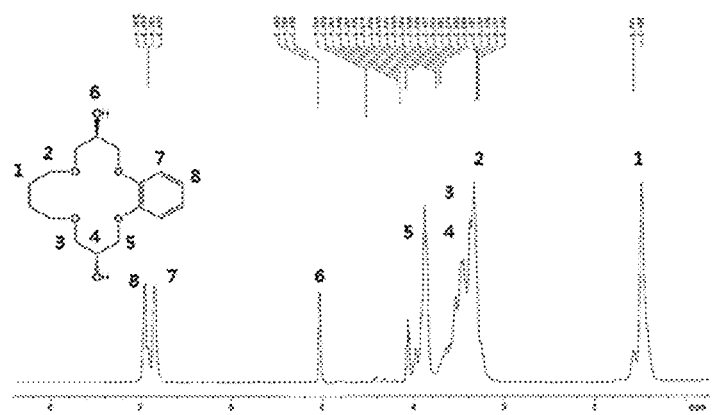
Figure 4:
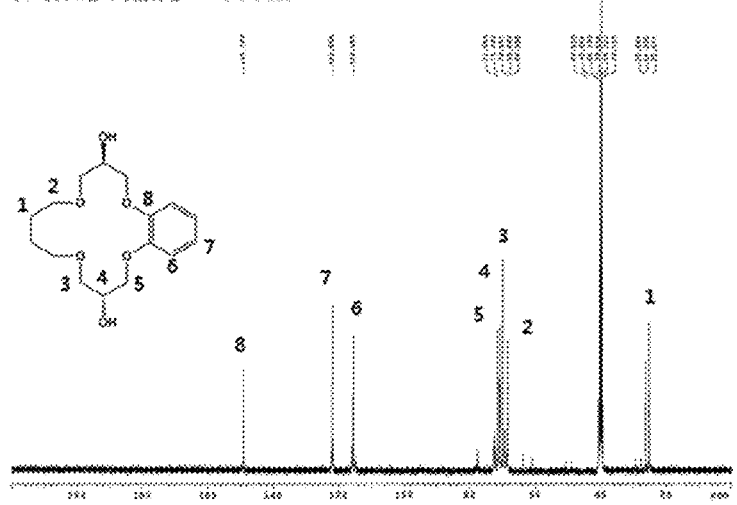
Figure 5:
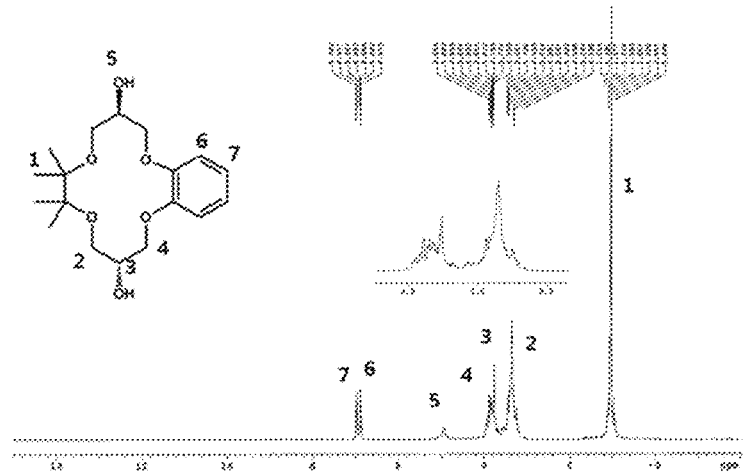
Figure 6:
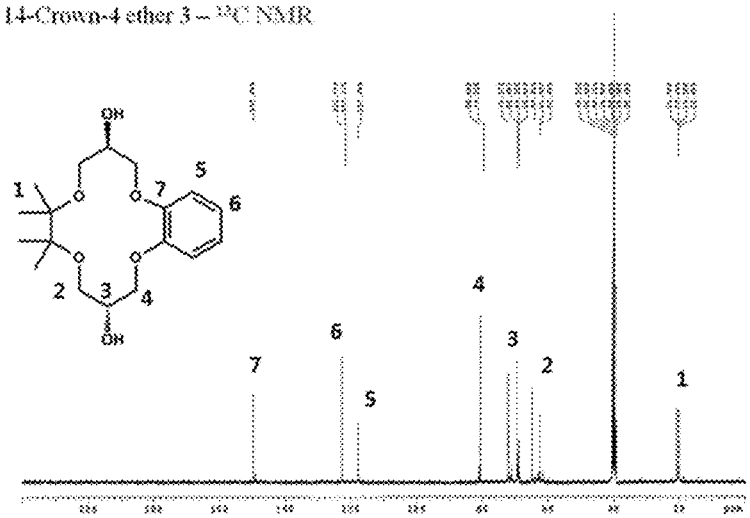
Figure 7:
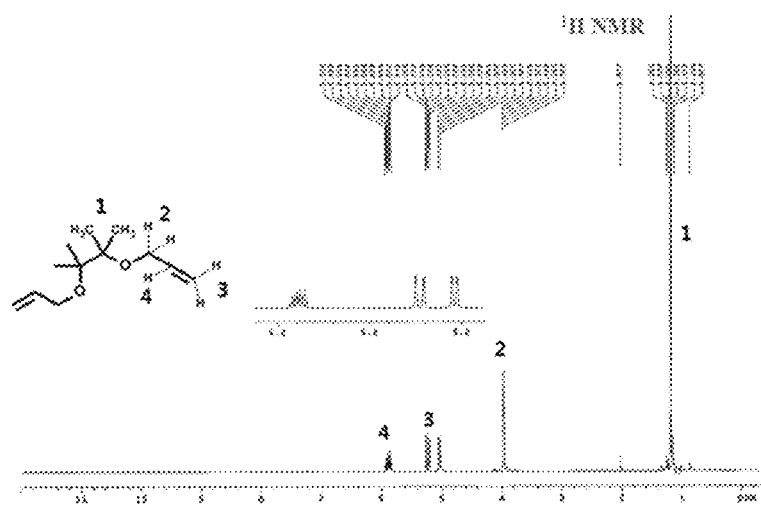
FIGS. 7 and 8 are $^1$H and $^{13}$C NMR spectra of a dialkene (2,3-M bis(allyloxy)-2,3-dimethylbutane) synthesized according to another exemplary embodiment of the present invention.
Figure 8:
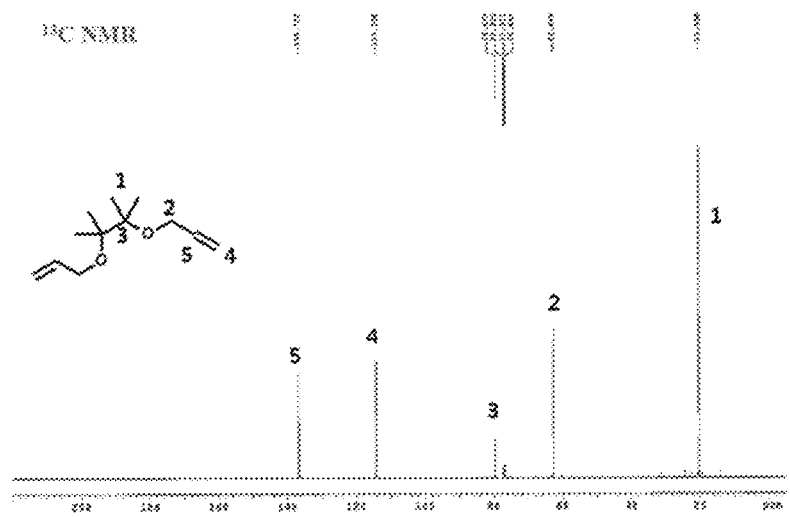
Figure 9:
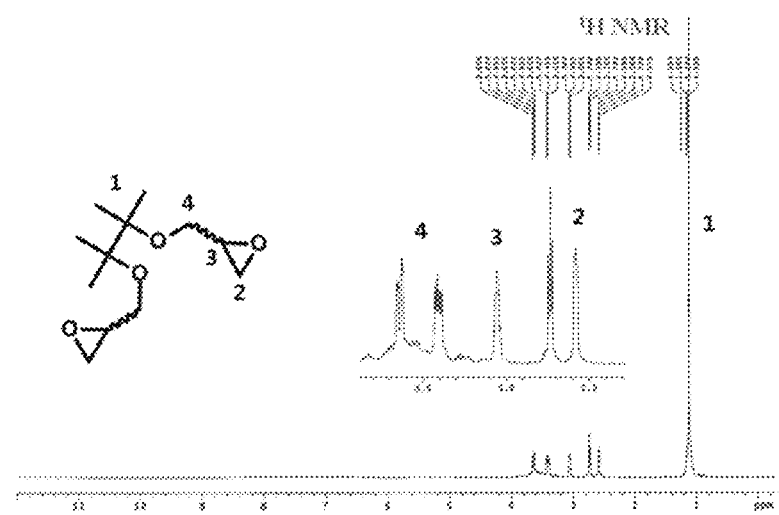
FIGS. 9 and 10 are $^1$H and $^{13}$C NMR spectra of bis-epoxide (2,2'-(2,3-dimethylbutane-2,3-diyl)bis(methylene) bis(oxirane)) synthesized according to another exemplary embodiment of the present invention.
Figure 10:
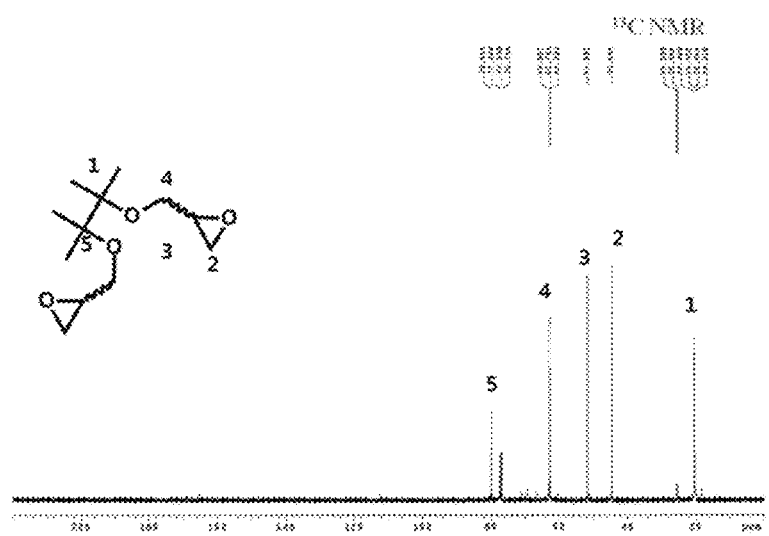
Figure 11:
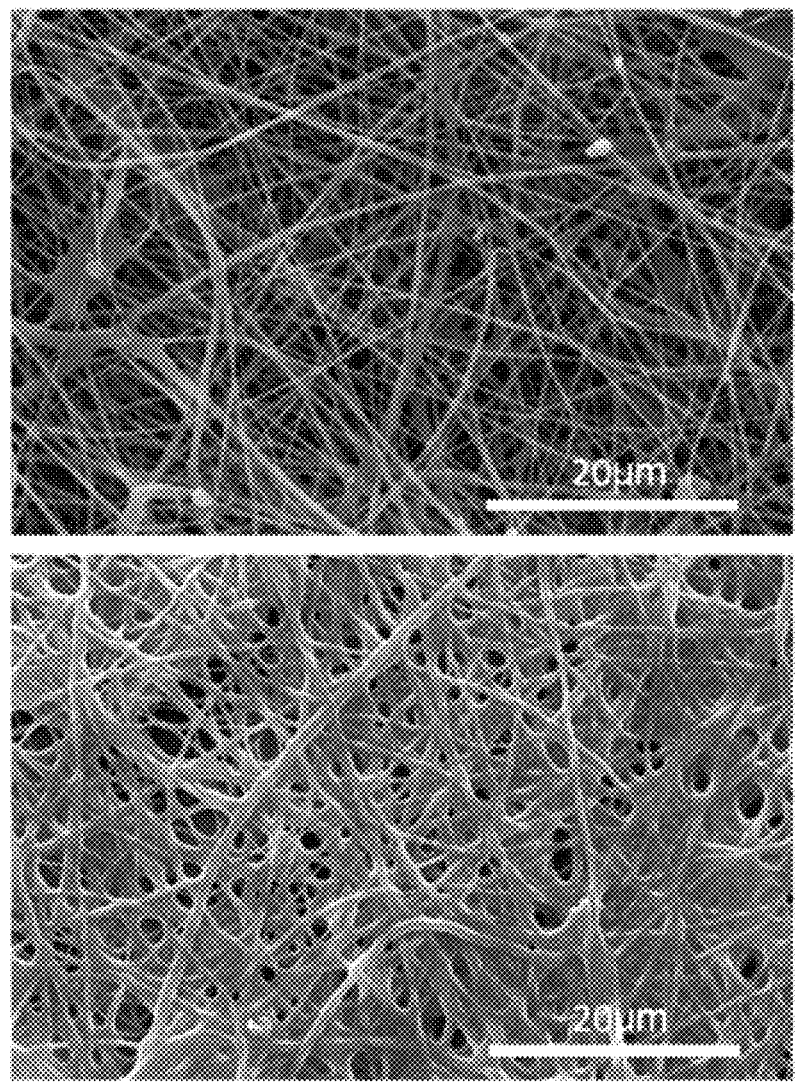
FIGS. 11 to 13 are SEM images of crown ether (CE11-PVA) immobilized onto a polymer nanofiber, uncrosslinked (upper panels) and crosslinked (lower panels), in accordance with one exemplary embodiment of the present invention.
Figure 12:
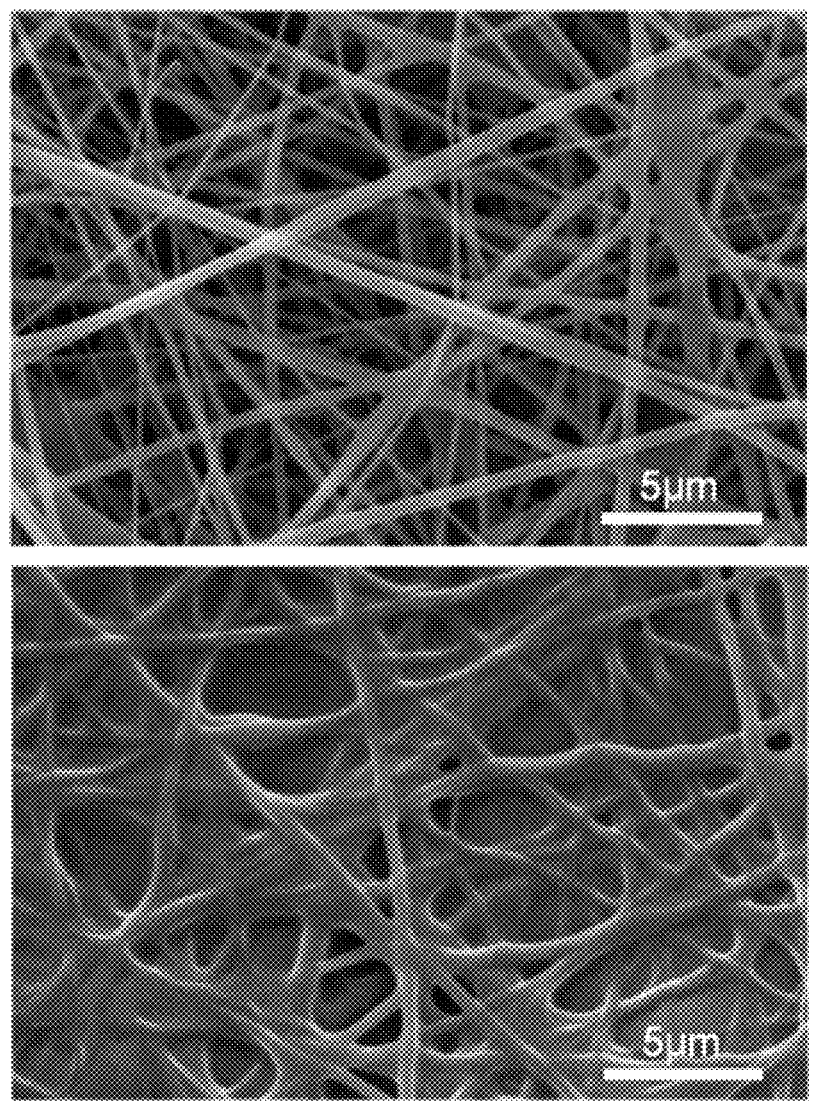
Figure 13:
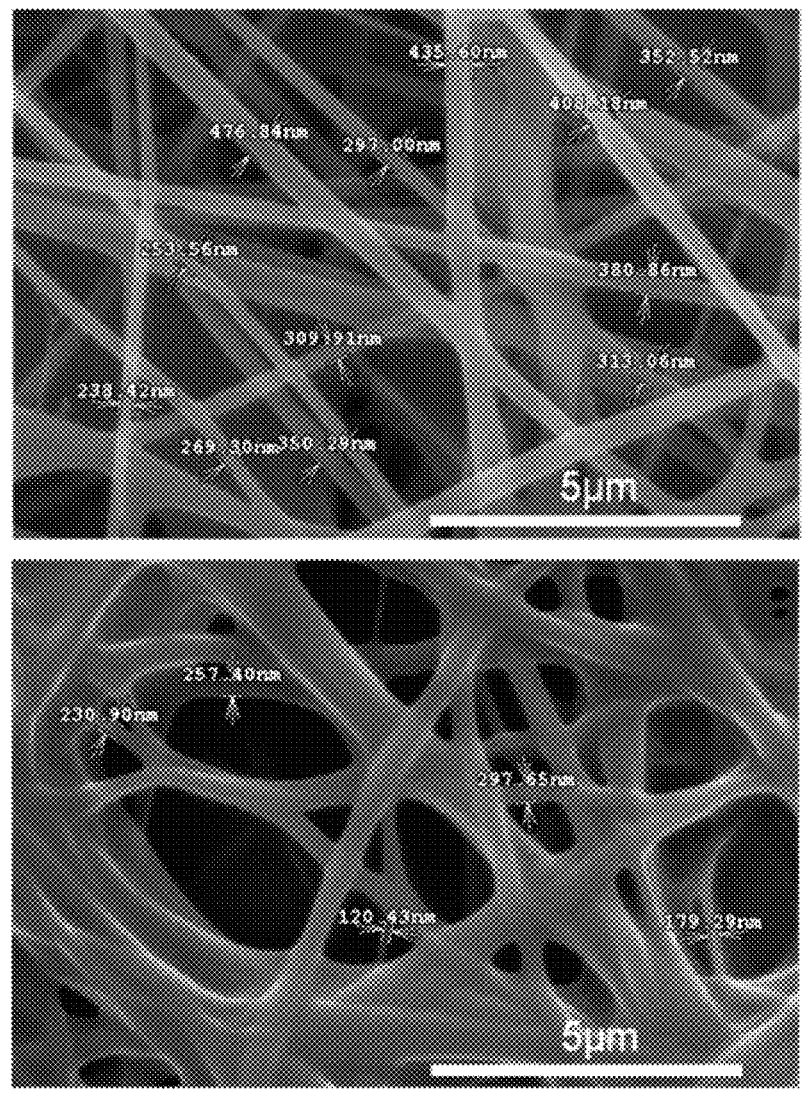
Figure 14:
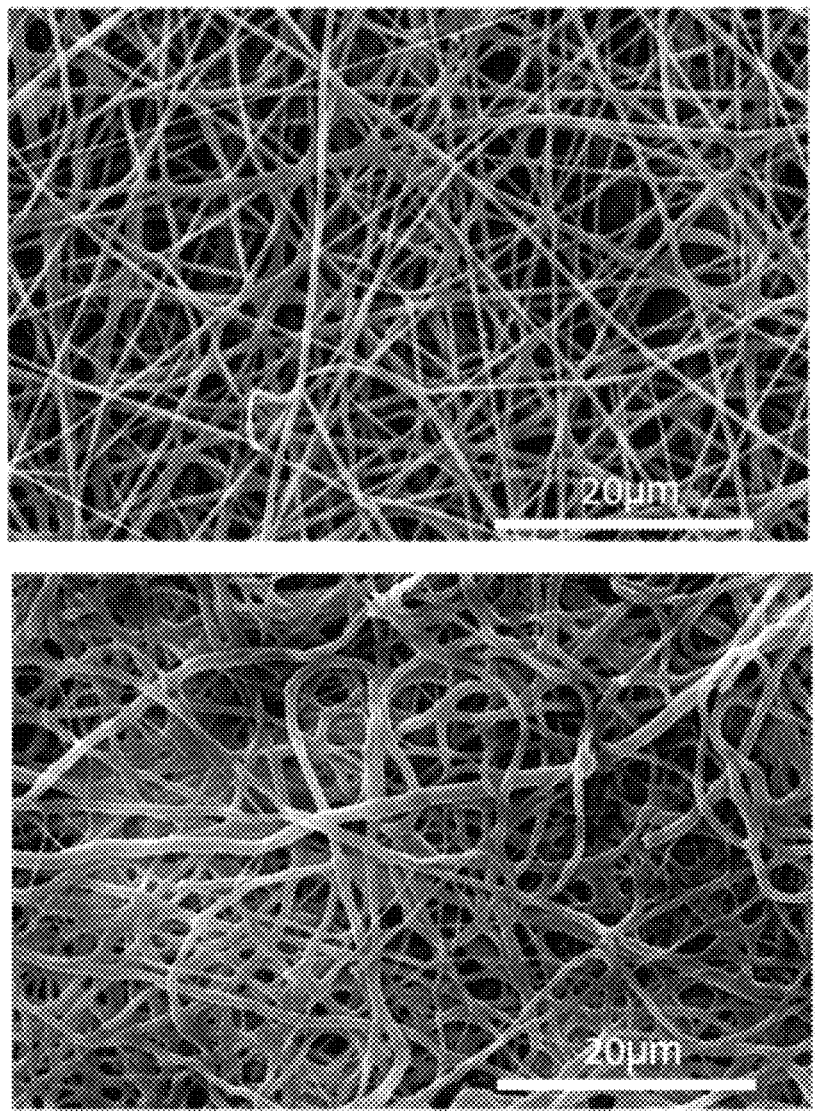
FIGS. 14 to 16 are SEM images of crown ether (CE12-PVA) immobilized onto a polymer nanofiber, uncrosslinked (upper panels) and crosslinked (lower panels), in accordance with one exemplary embodiment of the present invention.
Figure 15:
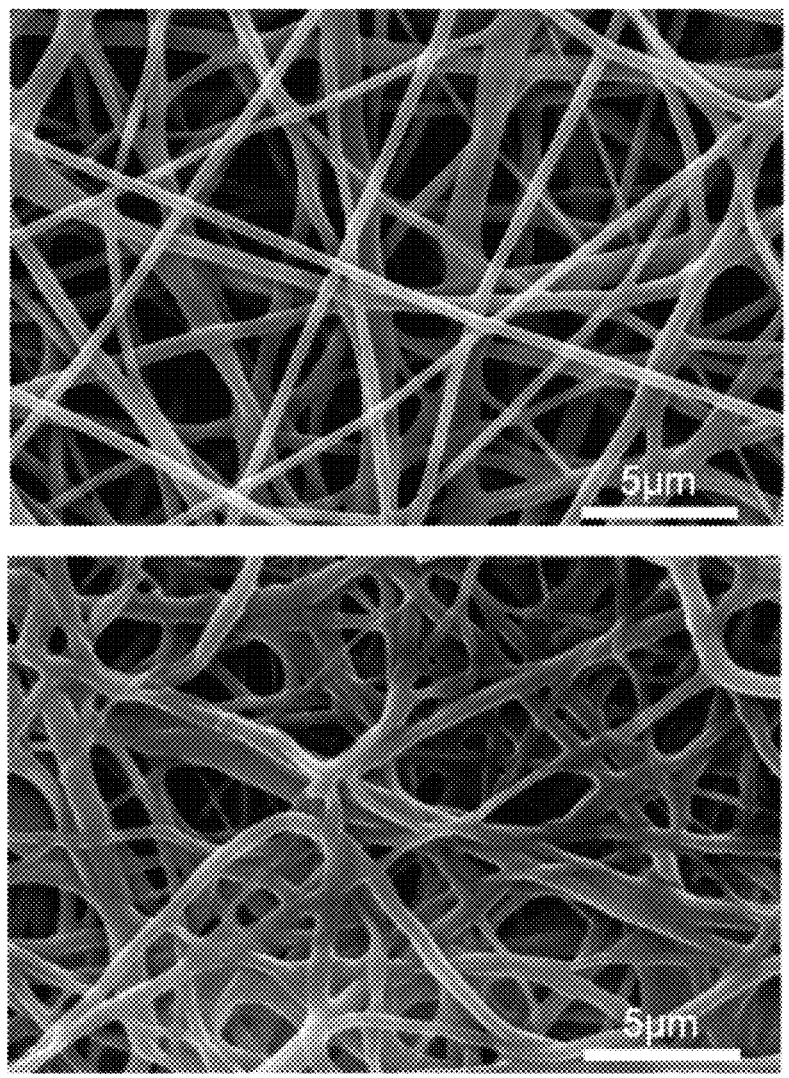
Figure 16:
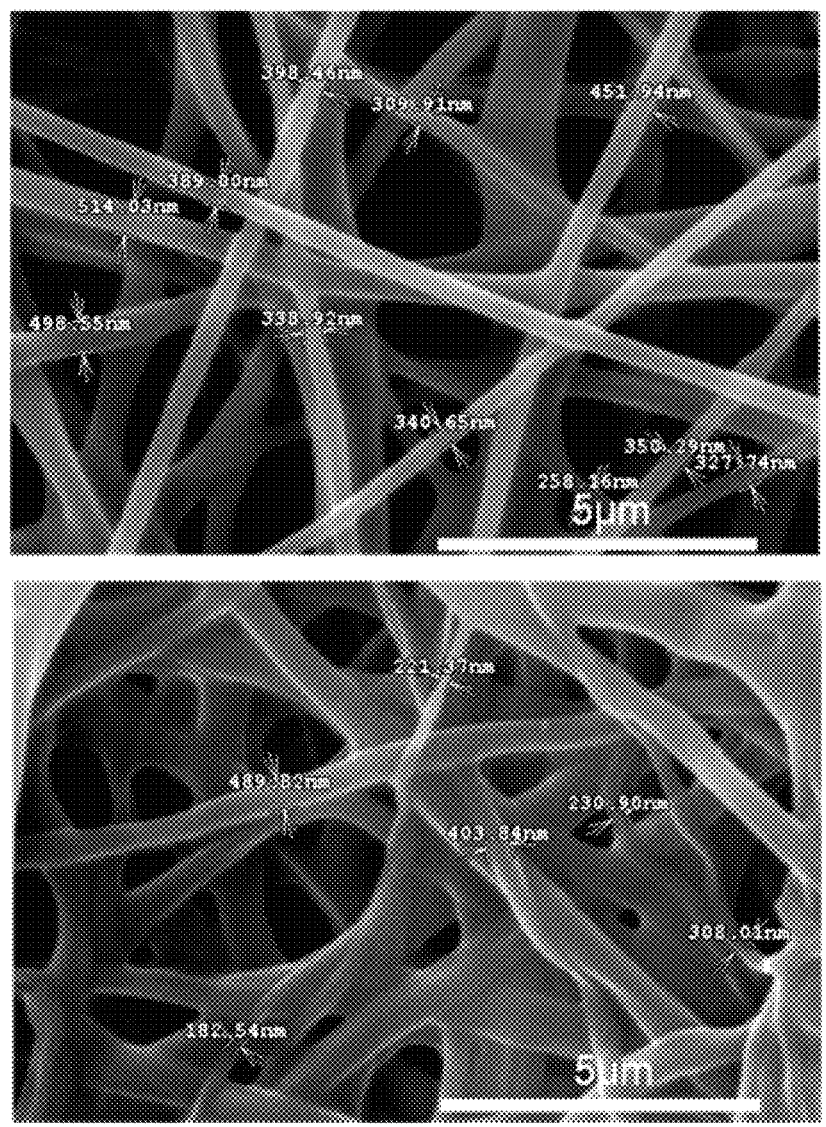

Hereinbelow, preferred embodiments of the present invention will be described in detail with reference to the accompanying drawings. However, it should be understood that the embodiment of the present invention may be changed to a variety of embodiments and the scope and spirit of the present invention are not limited to the embodiment described hereinbelow. The embodiment of the present invention described hereinbelow is provided for allowing those skilled in the art to more clearly comprehend the present invention. Therefore, it should be understood that the shape and size of the elements shown in the drawings may be exaggeratedly drawn to provide an easily understood description of the structure of the present invention.

A better understanding of the present invention may be obtained through the following examples which are set forth to illustrate, but are not to be construed as limiting the present invention.

Example 1: Synthesis of Dihydroxy-14-Crown-4 ether

Materials and Installment

Solvents, reagents, starting bulky diols, and bis-epoxides were purchased from Sigma-Aldrich Korea or Fischer Scientific. NaH was cleansed with pentane to remove protecting oil therefrom. A solution of m-chloroperbenzoic acid in ethyl ether was purified with a phosphate buffer to remove impurities. The other compounds were used without further purification. Novel compounds synthesized were identified by FTIR(Varian 2000) at 400 MHz and 100 MHz, and by $^1$H and $^{13}$C NMR (Varian, 400 MR Fourier Transform Nuclear Magnetic Resonance).

Synthesis of Di-alkene Intermediate

An equimolar diol solution was dissolved for 30 min in anhydrous THF (200 mL), and was then mixed at room temperature under an argon atmosphere. This mixture was added with allyl bromide (molar ratio of 1:2 diol:allyl bromide), stirred for 1 hr, and then refluxed for 24 hrs. The resulting solution was slowly quenched in water, and the solvent was removed in a vacuum, followed by washing the residue with water. The aqueous layer was extracted twice with dichloromethane, and the organic layers were washed, dried over MgSO$_4$, and concentrated. The concentrate was purified by silica gel column chromatography using ethyl acetate/hexane as an eluent.

Synthesis of Bis-Epoxide Intermediate

At 0° C., m-chloroperbenzoic acid (m-CPBA) was added to chloroform and stirred to give a solution to which a di-alkene intermediate dissolved for 30 min in dichloromethane was added (molar ratio of 1:2.5 di-alkene:m-CPBA). The resulting admixture was stirred at room temperature for 24 hrs, filtered, washed with 10% NaHCO$_3$, and then dried over MgSO$_4$. After the removal of the solvent in a vacuum, the residue was purified by silica gel chromatography using dichloromethane as an eluent.

Intramolecular Cyclization of Bis-epoxide with 1,2-Dihydroxybenzene

In a suitable solvent (50 mL/mmol substrate), 1,2-dihydroxybenzene and a suitable metal hydroxide were dissolved in equimolar amounts, and the solution was refluxed in an argon atmosphere. Then, the solution was added with bis-epoxide (molar ratio of 1:1 bis-epoxide:1,2-dihydroxybenzene) and stirred for 6 hrs. Subsequently, the metal hydroxide was further added in the same amount to the reaction mixture, stirred, and refluxed for 42 hrs. After the removal of the solvent by vacuum evaporation, the residue was dissolved in chloroform and washed with water. The aqueous layers were back-extracted with chloroform, and the chloroform layers dried over MgSO$_4$, filtered, and evaporated in a vacuum. The residue was dissolved in methanol and purified with alumina and silica using a mixture of ethylacetate/methanol as an eluent.

Analysis for Effect of Solvent and Template

To obtain an optimal experimental condition for the synthesis of di-hydroxy-functionalized crown ethers through the intermolecular cyclization of bis-epoxide with 1,2-dihydroxybenzene (see Reaction Scheme 1), tests were performed with various solvents and metal hydroxides (metal ion catalyst/template), and the results are given in Table 1, below. Table 1 summarizes the cyclization results using commercially available bis-epoxides. When t-BuOH and NaOH were used as a solvent and a catalyst/template, respectively, cyclized products were produced at a yield of 70%. Thanks to its good solvency for aromatic alkoxides such as 1,2-dihydroxybenzene, t-BuOH was believed to enhance the cyclization yield. In order to act as a template for facilitating the cyclization, the metal hydroxide catalyst is well suited to the size of a target crown ether. When used as a catalyst (template) for the reaction of 1, 2-dihydroxybenzene with neopentyl glycol diglycidyl ether, NaOH was observed to guarantee a higher yield than LiOH or KOH, which are smaller and larger in size than NaOH, respectively.

[Reaction Scheme 1]

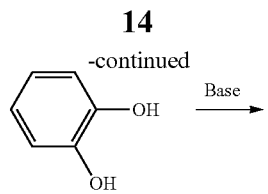

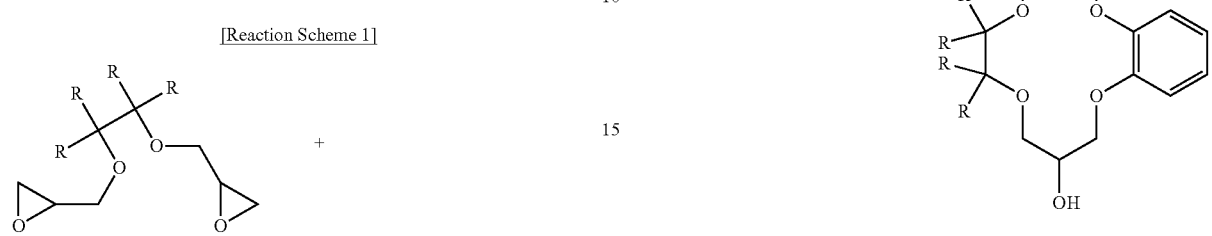

TABLE 1

Effects of Solvents and Template Ions

| Entry | Bis-epoxide | Solvent (reaction conditions)[a] | Catalyst/template | Product[b] | Isolated yield (%) |
|---|---|---|---|---|---|
| 1 | | t-BuOH (reflux, 24 h) | LiOH | | 67 |
| 2 | | t-BuOH (reflux, 24 h) | NaOH | | 70 |
| 3 | | t-BuOH (reflux, 48 h) | NaOH | | 68 |

TABLE 1-continued

Effects of Solvents and Template Ions

| Entry | Bis-epoxide | Solvent (reaction conditions)[a] | Catalyst/template | Product[b] | Isolated yield (%) |
|---|---|---|---|---|---|
| 4 | (bis-epoxide with gem-dimethyl) | t-BuOH (reflux, 24 h) | KOH | (benzo-crown ether diol) | 11 |
| 5 | (bis-epoxide with gem-dimethyl) | THF (rt, 24 h) | NaH | (benzo-crown ether diol) | trace[c] |
| 6 | (bis-epoxide with gem-dimethyl) | 1:1 v/v THF/H$_2$O (reflux, 24 h) | LiOH | (benzo-crown ether diol) | 23 |
| 7 | (bis-epoxide with gem-dimethyl) | 1:1 v/v THF/H$_2$O (reflux, 24 h) | NaOH | (benzo-crown ether diol) | 51 |

TABLE 1-continued

Effects of Solvents and Template Ions

| Entry | Bis-epoxide | Solvent (reaction conditions)[a] | Catalyst/template | Product[b] | Isolated yield (%) |
|---|---|---|---|---|---|
| 8 | (bis-epoxide structure) | t-BuOH (reflux, 24 h) | LiOH | (dihydroxy 14-crown-4 product) | 52 |
| 9 | (bis-epoxide structure) | t-BuOH (reflux, 24 h) | NaOH | (dihydroxy 14-crown-4 product) | 65 |
| 10 | (bis-epoxide structure) | t-BuOH (reflux, 24 h) | KOH | (dihydroxy 14-crown-4 product) | 62 |

[a] Reactions were performed at a molar ratio of 1:1 bis-epoxide: 1,2-dihydroxybenzene
[b] Structures were identified by $^1$H and $^{13}$C NMR
[c] Trace of target compound seen using TLC Synthesis of Bulky and Rigid 14-Crown-4 Ether By the intermolecular cyclization of a bulky bis-epoxide with 1,2-dihydroxybenzene, a dihydroxy functionalized 14-crown-4 ether having both bulky and rigid subunits was synthesized (see Reaction Scheme 2 and Table 2). Briefly, a dialkene intermediate was synthesized by reacting an allyl bromide with a bulky starting diol, and was then converted into a bis-epoxide containing bulky groups by epoxidizing the terminal alkenes with m-CPBA. Subsequently, the bis-epoxide was cyclized with 1,2-dihydroxybenzene to afford a bulky and rigid 14-crown-4 ether (see Reaction Scheme 2).

[Reaction Scheme 2]

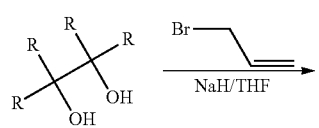

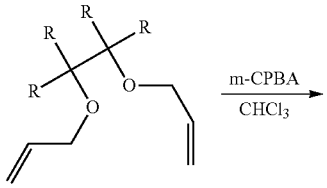

-continued

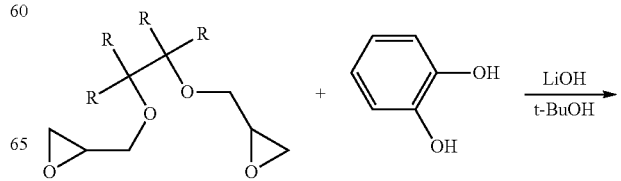

-continued

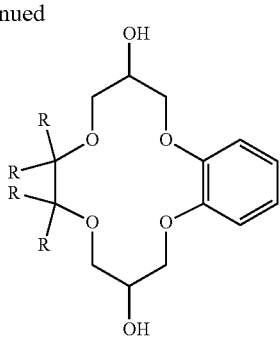

The results of synthesizing bulky and rigid 14-crown-4 ethers are summarized in Table 2, below. Through cyclization between bis-epoxide, having bulky subunits, and 1,2-dihydroxybenzene, 14-crown-4 ethers were synthesized at high yield. The synthesized bis-epoxides (diglycidyl ethers) were cyclized with 1,2-dihydroxybenzene. The resulting 14-crown-4 ethers varied in yield from 74 to 92% depending on the structures of the bis-epoxides. The overall yields of the dihydroxy-14-crown-4 ethers with bulky and rigid (hard) groups were higher than those of the neutral counterparts. This is attributed to the fact that 1,2-dihydroxybenezene has high activity as a nucleophile for the ring opening of bis-epoxide, which triggers the cyclization.

TABLE 2

Intermolecular cyclization of bulky bis-epoxide and 1,2-dihydroxybenzene

| Entry | Starting diol | Dialkene intermediate (isolated yield) | Diglycidyl ether intermediate (isolated yield) | Product crown ether (isolated yield) |
|---|---|---|---|---|
| 1 | Pinacol | (85%) | (90%) | (92%) |
| 2 | 2,2-Diethyl-1,3-Propanediol | (98%) | (80%) | (90%) |
| 3 | [1,1'-bicyclopentyl]-1,1'-diol | (95%) | (92%) | (92%) |

TABLE 2-continued

Intermolecular cyclization of bulky bis-epoxide and 1,2-dihydroxybenzene

| Entry | Starting diol | Dialkene intermediate (isolated yield) | Diglycidyl ether intermediate (isolated yield) | Product crown ether (isolated yield) |
|---|---|---|---|---|
| 4 | Cis-1,2-cyclohexanediol | (90%) | (94%) | (81%) |
| 5 | Cis-1,2-Cyclopentanediol | (92%) | (85%) | (74%) |

According to one embodiment of the present invention, intermolecular cyclization between bis-epoxide and 1,2-dihydroxybenzene allowed for the synthesis of dihydroxy functionalized 14-crown-4 ethers with both bulky and hard (rigid) groups at high yield. The novel crown ethers with both bulky and rigid groups were able to effectively recover lithium ions from sea water. For use in other applications, the novel crown ethers can be modified by changing the hydroxyl groups with other groups. By way of example, the hydroxyl groups may be substituted with groups suitable for immobilizing the crown ethers onto solid supports, so that the immobilized crown ethers can be used as sensing fluoroionophores, lithium battery electrolytes, or proton ionizable side arms for the liquid-liquid extraction of lithium or for the solid-liquid extraction of lithium.

Experimental Example 1: Structural Analysis of Synthesized Novel Compounds

The novel compounds synthesized above (see Table 2) were structurally identified by $^1$H and $^{13}$C NMR (Varian, 400 MR Fourier Transform Nuclear Magnetic Resonance) (FIGS. 1 to 10).

14-Crown-4 Ether 1

7,7-Dimethyl-3,4,6,7,8,10,11,12-octahydro-2H-benzo[1,4,8,12]tetraoxacyclopentadecine-3,11-diol

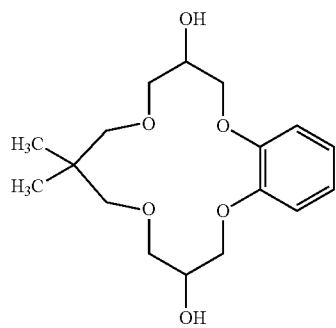 [SMILES: CC1(C)COCC(O)COc2ccccc2OCC(O)COC1]

Purification was performed by column chromatography using methanol/chloroform (5:1) as an eluent to afford the compound as a pale yellow viscous liquid. 3.1 g (70%).

$^1$H NMR (400 MHz, CDCl$_3$) δ(ppm): 0.72-0.81 (m, 6H, —CH$_3$; 3.03-3.21 (m, 4H, —CH$_2$—), 3.36-3.67 (m, 4H, —CH$_2$—), 3.79-4.06 (m, 6H, —CH$_2$—, —CH—), 4.95 (d, 2H, —OH); 6.73-7.02 (m, 4H, ArH).

$^{13}$C NMR (100 MHz, CDCl$_3$): δ(ppm) 22.62, 37.05, 67.70, 71.03, 72.87, 77.43, 77.54, 113.67, 115.89, 121.60, 122.59, 147.11.

14-Crown-4 Ether 2

2,3,4,6,7,8,9,11,12,13 Decahydrobenzo[1,4,8,13]tetraoxacyclohexadecine-3,12-diol

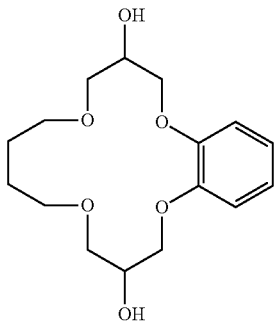 [SMILES: OC1COCCCCOCC(O)COc2ccccc2OC1]

Purification was performed by column chromatography using methanol/chloroform (8:1) as an eluent to afford the compound as a pale yellow viscous liquid. 2.2 g (65%).

$^1$HNMR (400 MHz, CDCl$_3$) δ(ppm): 1.49 (s, 4H, —CH$_2$—); 3.14-3.64 (m, 10H, —CH$_2$—, —CH—), 3.85-4.36 (m, 4H, —CH$_2$—), 4.94 (2, 2H, —OH), 6.85-6.96 (m, 4H, ArH).

$^{13}$C NMR (100 MHz, CDCl$_3$): δ(ppm) 25.07, 68.39, 69.84, 70.66, 71.45, 71.58, 115.49, 121.86, 149.10.

14-Crown-4 Ether 3

6,6,7,7-Tetramethyl-2,3,4,6,7,8,10,11-octahydrobenzo[1,4,8,11] tetraoxacyclotetradecine-3,10-diol)

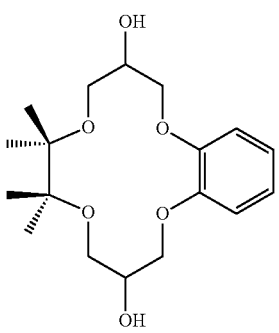

Purification was performed by column chromatography using dichloromethane as an eluent to afford the compound as a pale yellow viscous liquid. 1.2 g (85%).

$^1$H NMR (400 MHz, CDCl$_3$) δ(ppm): 1.06 (s, 12H, 4 —CH$_3$); 3.13-3.44 (m, 4H, —CH$_2$—), 3.76-3.89 (m, 5H, —CH$_2$—, —CH—), 4.82 (s, 2H, —OH), 6.87-6.38 (m, 4H, ArH).

$^{13}$C NMR (100 MHz, CDCl$_3$): δ(ppm) 20.24, 20.76, 62.44, 64.31, 69.15, 72.17, 78.59, 117.77, 121.58, 149.65.

Intermediate 1a:

2,3-Bis(allyloxy)-2,3-dimethylbutane

Purification was performed by column chromatography using hexane/ethyl acetate (2:1) as an eluent to afford the compound as a clear liquid. 10.7 g (85%).

$^1$H NMR (400 MHz, CDCl$_3$) δ(ppm): 1.18 (s, 12H, 4-CH$_3$); 3.97 (d, 4H, —CH$_2$), 5.03-5.06 (dd, 2H, =CH$_2$), 5.20-5.26 (dd, 2H, =CH$_2$), 5.84-5.93 (m, 2H, CH=CH$_2$).

$^{13}$C NMR (100 MHz, CDCl$_3$): δ(ppm) 20.41, 62.86, 79.67, 114.21, 136.722.

Intermediate 2a:

3,3-Bis(allyloxy)methylpentane

Purification was performed by column chromatography using hexane/ethyl acetate (2:1) as an eluent to afford the compound as a clear liquid. 13.21 g (98%).

$^1$H NMR (400 MHz, CDCl$_3$) δ(ppm): 0.78 (t, 6H, 2-CH$_3$); 1.58 (q, 4H, —CH$_2$—), 3.20 (s, 4H, —CH$_2$—), 3.91-3.93 (m, 4H, —CH$_2$—), 5.10-5.13 (dd, 2H, =CH$_2$), 5.21-5.26 (m, 2H, =CH$_2$), 5.82-5.92 (m, 2H, CH=CH$_2$).

$^{13}$C NMR (100 MHz, CDCl$_3$): δ(ppm) 7.22, 23.26, 40.99, 72.13, 72.21, 116, 135.39.

Intermediate 3a:

1,1'-Bis(allyloxy)-1,1'bi(cyclopentane)

Purification was performed by column chromatography using hexane/ethyl acetate (3:1) as an eluent to afford the compound as a clear liquid. 7.35 g (95%)

$^1$H NMR (400 MHz, CDCl$_3$) δ(ppm): 0.78 (t, 6H, 2-CH$_3$; 1.51-1.82 (m, 16H, 8CH$_2$—), 3.97-3.99 (dd, 4H, 2-CH$_2$—), 5.0-5.08 (m, 2H, =CH$_2$), 5.18-5.25 (m, 2H, =CH$_2$), 5.82-5.91 (m, 2H, CH=CH$_2$).

$^{13}$C NMR (100 MHz, CDCl$_3$): δ(ppm) 26.44, 32.63, 66.94, 92.58, 114.18, 136.66.

Intermediate 4a:

1,2-Bis(allyloxy)cyclohexane

Purification was performed by column chromatography using hexane/ethyl acetate (3:1) as an eluent to afford the compound as a clear liquid. 8.44 g (90)

$^1$H NMR (400 MHz, CDCl$_3$) δ(ppm): 0.83-1.27 (m, 2H, —CH$_2$—), 1.37-1.43 (m, 2H, —CH$_2$—), 1.54-1.61 (m, 2H, —CH$_2$—), 1.77-1.84 (m, 2H, —CH$_2$—), 3.46-3.48 (dd, 2H, —CH—), 4.0-4.07 (dd, 4H, 2-CH$_2$—), 5.06-5.10 (m, 2H, =CH$_2$), 5.19-5.25 (m, 2H, =CH$_2$), 5.83-5.93 (m, 2H, CH=CH$_2$).

$^{13}$C NMR (100 MHz, CDCl$_2$): δ(ppm) 27.62, 69.56, 70.02, 116.11, 135.72.

Intermediate 5a:

1,2-Bis(allyloxy)cyclopentane

Purification was performed by column chromatography using hexane/ethyl acetate (3:1) as an eluent to afford the compound as a clear liquid. 8.92 g (92-6).

$^1$H NMR (400 MHz, CDCl3) δ(ppm): 1.17-1.40 (m, 1H, —CH$_2$—), 1.41-1.44 (m, 1H, —CH$_2$—), 1.68-1.1.97 (m, 4H, —CH$_2$—), 3.71-3.77 (m, 2H, —CH—), 3.98-4.05 (dd, 4H, 2-CH$_2$—), 5.06-5.10 (m, 2H, =CH$_2$) 5.18-5.24 (m, 2H, =CH$_2$), 5.83-5.92 (m, 2H, CH=CH$_2$).

$^{13}$C NMR (100 MHz, CDCl$_3$): δ(ppm) 18.91, 27.95, 70.41, 79.76, 116.39, 135.38.

Intermediate 1b:

2,2'-(2,3-Dimethylbutane-2,3-diyl)bis(methylene)bis(oxirane)

Purification was performed by column chromatography using hexane/ethyl acetate (3:1) as an eluent to afford the compound as a clear liquid. 4.2 g (90%)

¹H NMR (400 MHz, CDCl₃) δ(ppm): 1.15 (s, 12H, 4 —CH₃); 2.58 (dd, J=4.8, 1.2 Hz, 4H, —CH₂), 2.74 (t, J=4.8 Hz, 2H, —CH₂—), 3.04-3.07 (m, 2H, —CH—), 3.39-3.43 (m, 2H, —CH₂—), 3.52-3.66 (m, 2H, —CH₂—).

¹³C NMR (100 MHz, CDCl₃): δ(ppm) 20.45, 44.64, 51.63, 62.75, 79.91.

Intermediate 2b:

2,2'-(2,2-Diethylpropane-1,3-diyl)bis(oxy) bis(methylene) bis(oxirane)

Purification was performed by column chromatography using dichloromethane as an eluent to afford the compound as a clear liquid. 3.7 g (80%).

¹H NMR (400 MHz, CDCl₃) δ(ppm): 0.753 (t, 6H, J=7.6, 2 —CH₃); 1.23 (p, J=7.6, 4H, —CH₂), 2.55-2.57 (m, 2H, —CH—), 2.73-2.76 (m, 2H, —CH—), 3.07-3.11 (m, 2H, —CH—), 3.23-3.53 (m, 4H, —CH₂—), 3.64-3.67 (m, 4H, —CH₂—).

¹³C NMR (100 MHz, CDCl₃): δ(ppm) 7.12, 7.16, 23.0, 41.19, 44.18, 51.03, 71.75, 71.78, 73.19.

Intermediate 3b:

1,1'-Bis(oxiran-2-ylmethoxy)-1,1'-bi(cyclopentane)

Purification was performed by column chromatography using dichloromethane as an eluent to afford the compound as a clear liquid. 2.08 g (92%)

¹H NMR (400 MHz, CDCl₃) δ(ppm): 1.20-2.01 (m, 16H, 4 —CH₃); 2.58-2.60 (m, J=7.2, 2.8, 2.4, 1.2 Hz, 2H, —CH₂), 2.73 (t, 2H, —CH₂), 3.04-3.07 (m, J=2.4, 1.2 Hz, 2H, —CH—), 3.41-3.46 (m, J=2.8, 2.4 Hz, 2H, —CH—), 3.67 (dd, J=2.8, 2.4 Hz, 2H, —CH—), 4.08 (p, J=7.2 Hz, 2H, —CH—).

¹³C NMR (100 MHz, CDCl₃): δ(ppm) 25.20, 35.41, 44.61, 44.62, 51.72, 63.57, 63.66, 92.83.

Intermediate 4b:

1,2-Bis(oxiran-2-ylmethoxy)cyclohexane

Purification was performed by column chromatography using dichloromethane as an eluent to afford the compound as a clear liquid. 3.85 g (94°).

¹H NMR (400 MHz, CDCl₃) δ(ppm): 0.79-0.85 (m, J=6.8, 6.4 Hz, 1H, 4 —CH—); 1.21 (s, 4H, 2-CH₂), 1.44-1.47 (m, J=6.8 Hz, 1H, —CH—), 1.70-1.79 (m, J=6.4 Hz, 4H, —CH₂—), 2.56-2.59 (m, J=2.8, 2.4 Hz, 2H, —CH₂—), 2.74-3.12 (m, J=4.4 Hz, 4 Hz, 2H, —CH₂—), 3.13-3.15 (m, J=4.2, 4 Hz, 2H, —CH—), 3.41-3.50 (m, 2H, —CH₂—), 3.73-3.84 (m, 2H, —CH₂—).

¹³C NMR (100 MHz, CDCl₃): δ(ppm) 14.01, 28.27, 28.58, 44.30, 44.30, 44.34, 44.47, 44.49, 51.06, 70.18, 70.25, 70.39, 70.50, 81.13, 81.21.

Intermediate 5b:

1,2-Bis(oxiran-2-ylmethoxy)cyclopentane

Purification was performed by column chromatography using dichloromethane as an eluent to afford the compound as a clear liquid. 4.4 g (85%).

¹H NMR (400 MHz, CDCl₃) δ(ppm): 1.18-1.23 (m, J=7.2, 3.6 Hz, 2H, —CH₂—); 1.39-1.46 (m, J=9, 2 Hz, 2H, —CH₂), 1.54-1.62 (m, J=9.2, 6 Hz, 2H, —CH₂—), 1.75-1.84 (m, J=9.2, 6 Hz, 2H, —CH₂—), 2.56-2.59 (m, J=2.8, 2.4 Hz, 2H, —CH₂—), 2.71-2.74 (m, J=4. 4 Hz, 4 Hz, 2H, —CH₂—), 3.08-3.12 (m, 2H, —CH—), 3.40-3.53 (m, 2H, —CH₂—), 3.71-3.79 (m, 2H, —CH₂—).

¹³C NMR (100 MHz, CDCl₃): δ(ppm) 14.10, 20.93, 21.87, 44.15, 44.26, 44.41, 44.43, 53.40, 63.63.

Example 2: Preparation of Crown Ethers Immobilized onto Polymer Support

The crown ethers in Table 3, prepared as described above, were used.

TABLE 3

| Crown Ether(CE) | | Note |
|---|---|---|
| CE11 | [structure: dihydroxy-14-crown-4 ether with gem-dimethyl and benzo subunits] | Dihydroxy-14-crown-4 ether with rigid and bulky subunits |
| CE12 | [structure: dihydroxy-14-crown-4 ether with benzo subunit] | Dihydroxy-14-crown-4 ether with rigid and bulky subunits |
| CE13 | [structure: dihydroxy dibenzo-14-crown-4 ether] | Dihydroxy dibenzo-14-crown-4 ether |

For use as a polymer support, polyvinyl alcohol (PVA, 98-99% hydrolyzed, typical average MW=85000-124000 g/mole) was purchased from Sigma-Aldrich (USA). Triton® X-100, purchased from Acros-Organics (USA), was used as a surfactant.

Glutaraldehyde (grade II, 25% in H₂O) was used as a crosslinker in a crosslinking solution, and was purchased from Sigma-Aldrich (USA). A heavy metal grade of hydrochloric acid (HCl, RHM 35-37%) was used as a catalyst while acetone (HPLC solvent, J. T. Baker, USA) was used as a solvent. For use in adsorption experiments, a lithium solution was prepared of lithium hydroxide (LiOH, ≥98%) from Sigma-Aldrich (Mo., USA), and lithium chloride (LiCl, ≥98%) from Fluka. All of the chemicals were used without further purification.

Crown Ether-Polyvinyl Alcohol (CE-PVA) Nanofiber Electrospinning

For use in preparing CE-PVA nanofibers, a dop solution was obtained by heating a predetermined amount of crown ether to 90° C. in deionized water while magnetically stirring, and then dissolving PVA powder (MW=85,000-124,000; 98-99% hydrolyzed) at 90° C. for 4 hrs in the CE solution while stirring with a magnet. The crown ether was loaded in an amount of 50 wt % with respect to the PVA polymer support. Subsequently, the dope solution was cooled to room temperature, mixed with a surfactant (Triton X-100, 0.7 v/w %) to reduce the surface tension, and stirred for 1 hr before electrospinning. Electrospinning was performed under the following conditions.

As shown in Table 4, below, three CE-PVA nanofibers were prepared. In this regard, 12 ml of a dope solution was spun at a predetermined speed from an electrospinning machine (Model: ESP200D/ESP100D, NanoNC Co., Ltd., South Korea) with the aid of a syringe pump (KD Scientific 750, South Korea). A predetermined DC voltage was applied between a metal nozzle and a rotating, aluminum foil-wrapped stainless steel drum while nanofibers were taken at a predetermined collector speed. The electrospinning parameters for CE-PVA nanofiber preparation are summarized in Table 4.

TABLE 4

Electrospinning Parameters for CE-PVA Nanofiber Preparation

| Parameters | CE 11-PVA | CE 12-PVA | CE 13-PVA |
|---|---|---|---|
| Syringe pumping speed (mL/h) | 2 | 2 | 1.5 |
| Voltage (kV) | 24-26 | 24-26 | 24-26 |
| Needle size (mm) | 0.21GA | 0.21GA | 0.19GB |
| Distance between needle and collector (mm) | 120 | 120 | 120 |
| Collector speed (rpm) | 235 | 235 | 235 |
| Electrospun amount (mL) | 10-15 | 10-15 | 10-15 |

For comparison with CE-PVA nanofibers, PVA nanofibers were prepared. A predetermined amount of PVA (MW=85,000-124,000; 98-99% hydrolyzed) was dissolved at 90° C. for 4 hrs in deionized water while being magnetically stirred. The dope solution thus obtained was cooled to room temperature, the surface tension thereof was reduced using a surfactant, and the solution was then stirred for 1 before electrospinning. Electrospinning was performed under the following conditions (see Table 5).

TABLE 5

Electrospinning Parameters for PVA Nanofiber Preparation

| Parameters | PVA dope solution |
|---|---|
| Syringe pumping speed (mL/h) | 0.1 |
| Voltage (kV) | 27-28 |
| Needle size (mm) | 0.21 |
| Distance between needle and collector (mm) | 100 |
| Collector speed (rpm) | 235 |
| Electrospun amount (mL) | 7-8.5 |

CE-PVA Nanofiber Crosslinking

CE-PVA nanofibers were chemically crosslinked by an aerosol method using acid-catalyzed glutaraldehyde in an acetone solution. A solution of glutaraldehyde (10 vol. %) and HCl (1 vol. %) in acetone was introduced into a polypropylene sprayer. Three aluminum foil-wrapped nanofiber strips (each having dimensions of 2×1 inches) were prepared by CE-PVA type, and one side of each strip was exposed by removing the aluminum foil. The strips were arranged in a row by CE-PVA type, and immobilized on acid-washed glass using double-sided tape attached to the rear aluminum foil side. In order to prevent the crosslinking solution from dripping from one row to another, a sheet of Kimtech® tissue was placed between the rows. After immobilization of the strips, the glass for supporting the nanofibers was mounted on a 45°-angle stand. Then, the complete wetting of the nanofiber strips was achieved by spraying the crosslinking solution three times over the nanofiber strips before drying the nanofibers for 15 min in air. Unless otherwise stated, the crosslinked nanofibers were washed with deionized water to remove glutaraldehyde and HCl, dried in air, and stored in an acid-containing petri dish until use.

In one embodiment of the present invention, the crown ethers with both bulky and rigid subunits can be immobilized by directly mixing with a PVA dope solution. Subsequently, the CE-PVA dope solution is electrospun to produce nanofibers which are then crosslinked using a solution of acid-catalyzed glutaraldehyde in acetone.

All the crown ethers were observed to be dissolved in acetone as measured by a dissolution test. To exclude the possibility of the loss of crown ethers from the materials, the nanofibers were crosslinked by an aerosol method. In this regard, a nanofiber sample was suspended from acid-washed glass on a 45°-angled stand, and the crosslinking solution was sprayed over the nanofiber sample.

Experimental Example 2: Characterization of Crosslinked Nanofibers

Examination was made of the effect of aerosol crosslinking on the nanofibers. First, nanofibers were weighed before and after crosslinking using a high precision analytical balance. The CE-PVA nanofibers (Pt-coated) were analyzed for surface morphology by SEM-EDX (Scanning Electron Microscope equipped with Energy Dispersive X-ray Spectrometer, Hitachi S-3500 N, Japan). FTIR (Fourier Transform Infrared Spectroscopy) was used to examine the immobilization of crown ethers on a PVA polymer support and the crosslinking of the nanofibers with glutaraldehyde.

Analysis of Weights Before and after Crosslinking

To examine whether the crosslinking was achieved without loss of the crown ethers, the weights of the nanofibers were analyzed before and after crosslinking. In Table 6, the pre- and post-crosslinking weights of nanofiber samples are summarized.

TABLE 6

| Nanofiber | Trial | Before Crosslinking (g) | After Crosslinking (g) | Difference (g) |
|---|---|---|---|---|
| CE11-PVA | 1 | 0.0103 | 0.0114 | 0.0011 |
| CE11-PVA | 2 | 0.0105 | 0.0152 | 0.0047 |
| CE11-PVA | 3 | 0.0549 | 0.0581 | 0.0032 |
| CE12-PVA | 1 | 0.0556 | 0.06 | 0.0044 |
| CE12-PVA | 2 | 0.0522 | 0.0767 | 0.0245 |
| CE12-PVA | 3 | 0.0122 | 0.0176 | 0.0054 |
| CE13-PVA | 1 | 0.0362 | 0.0488 | 0.0126 |
| CE13-PVA | 2 | 0.0472 | 0.0549 | 0.0077 |
| CE13-PVA | 3 | 0.0405 | 0.0472 | 0.0067 |
| Pure PVA | 1 | 0.0178 | 0.0225 | 0.0047 |
| Pure PVA | 2 | 0.0183 | 0.0218 | 0.0035 |
| Pure PVA | 3 | 0.0179 | 0.0222 | 0.0043 |

As shown in Table 6, all the CE-PVA nanofiber strips gained weight after crosslinking, and none of the materials (i.e., crown ethers) lost weight even after washing with deionized water.

Morphological Analysis with SEM Image

Figure 21:
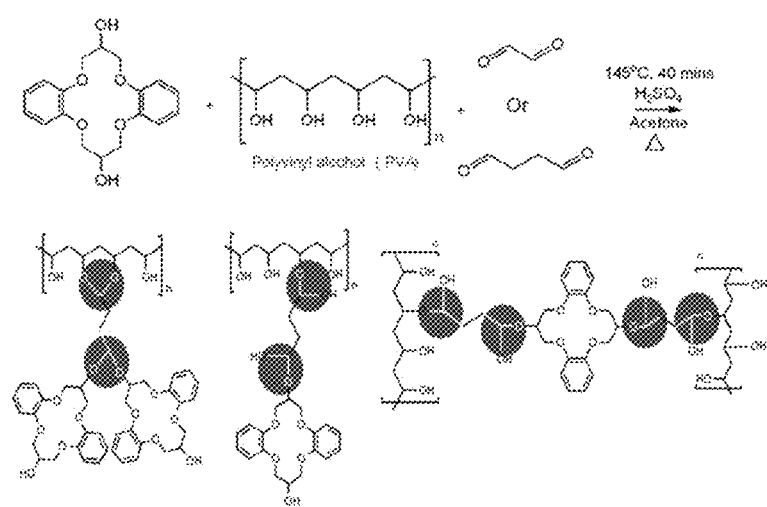
FIG. 21 shows a reaction mechanism of crosslinking between PVA and Crown Ether via Glutaraldehyde.

In one embodiment of the present invention, an electrospinning technique by which various types of polymeric binders can be employed was used to form nanofibers with micron- or sub-micron-scale diameters. In addition, chemical crosslinking was conducted between CE and PVA through acid-catalyzed glutaraldehyde (GA) in order to enhance the chemical and mechanical stability of PVA, which is water soluble. FIG. 21 shows a reaction mechanism of crosslinking between PVA and Crown Ether via Glutaraldehyde. As illustrated in FIG. 21, an acetal bridge is formed between the hydroxyl group of PVA and dihydroxy crown ether.

Since the crosslinking effect of glutaraldehyde becomes more potent in acetone, and since a high degree of crosslinking is required for the water-soluble polymer support, acetone was employed as the reaction medium in one embodiment of the present invention. Due to the solubility of crown ethers in acetone, however, a novel crosslinking method by which glutaraldehyde can be effectively introduced as a crosslinker into the material without dissolving crown ether is needed. In full consideration of this situation, an aerosol method was employed in which the crosslinking solution was sprayed over the material. Upon crosslinking using the aerosol method, the morphological changes of the nanofibers were examined, and the results are depicted in FIGS. 11 to 16. FIGS. 11 to 16 are SEM images of nanofibers that are not yet crosslinked (upper panels) and are crosslinked (lower panels). The crosslinker glutaraldehyde was observed to react with PVA fibers to form thicker fiber aggregates.

FTIR Analysis

FTIR analysis was conducted to check for success in the immobilization of crown ethers and in the crosslinking of polymer nanofibers.

Figure 17:
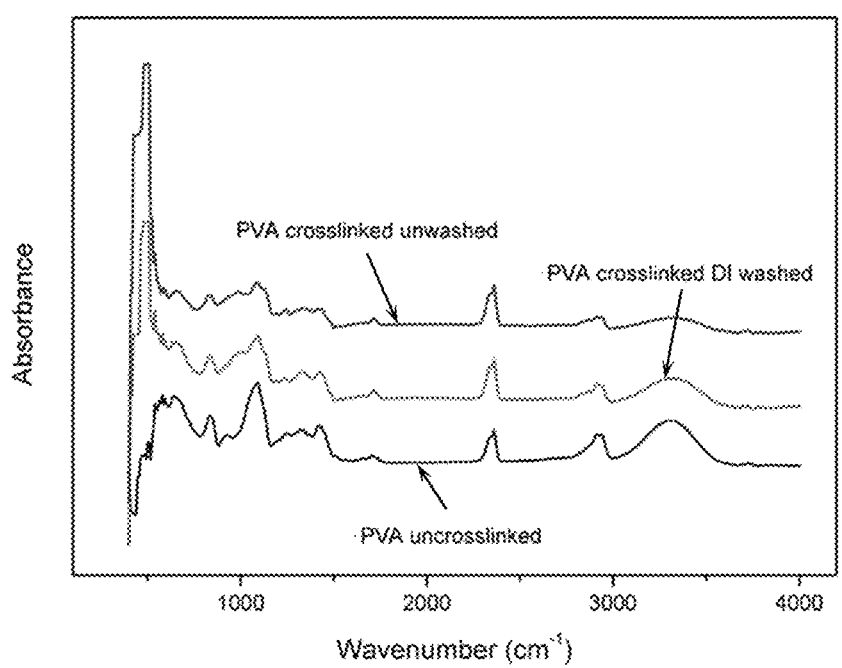
FIG. 17 shows FTIR spectra of pure PVA nanofibers.

FIG. 17 shows the FTIR spectra of pure PVA and glutaraldehyde-linked PVA. The 0-H stretching vibration band at 3350 cm-1 of uncrosslinked pure PVA was decreased along with the slight band shift to a higher wavenumber for the crosslinked (both unwashed and DI washed) PVA nanofiber. This data resulted from a reduced number of OH groups, indicating that the crosslinked PVA was weaker in hydrogen bond intensity than pure PVA. Also, a reduced hydroxy C—O stretching band was read at 1090 $cm^{-1}$ on the pure PVA spectrum, and an absorption band was read at 980 $cm^{-1}$, which might be attributed to ether C—O and acetal ring C—O stretching bands. This FTIR analysis confirmed the presence of OH, —O—, and —CHO groups in the PVA membrane crosslinked by glutaraldehyde. Taken together, the data obtained above implies that the polymer nanofibers were successfully crosslinked through glutaraldehyde.

Figure 18:
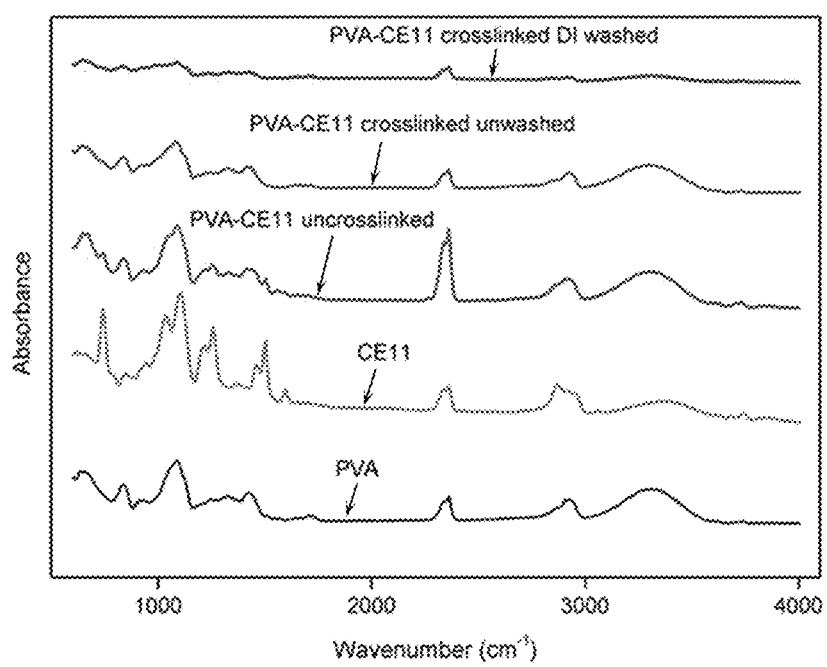
FIG. 18 shows FTIR spectra of the crown ether (CE11-PVA) immobilized onto a polymer nanofiber in accordance with an exemplary embodiment of the present invention.
Figure 19:
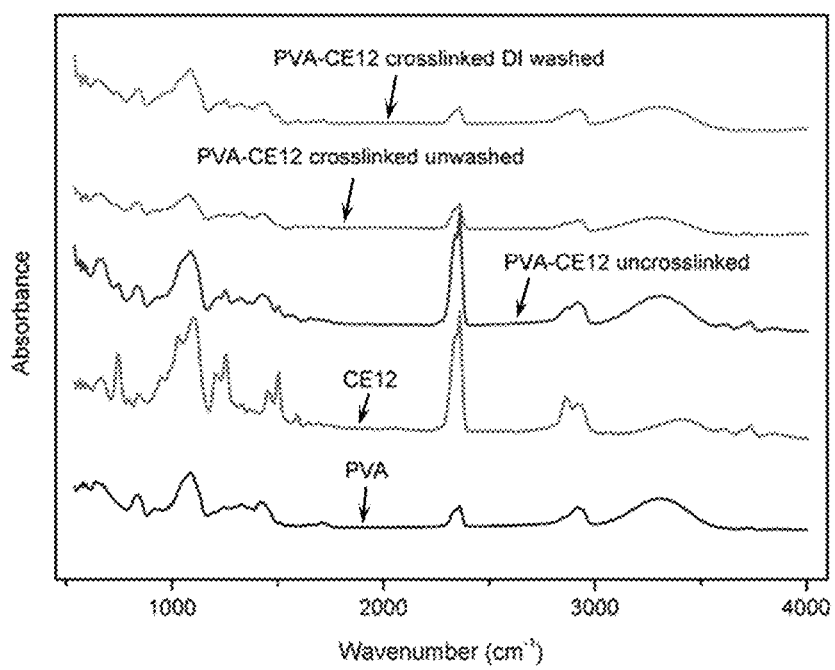
FIG. 19 shows FTIR spectra of the crown ether (CE12-PVA) immobilized onto a polymer nanofiber in accordance with an exemplary embodiment of the present invention.

FIGS. 18 and 19 are FTIR spectra of CE11-PVA and CE12-PVA nanofibers, respectively. As can be seen, absorption bands of pure crown ethers, although undergoing slight shifts and changes, still remained in the crosslinked CE-PVA nanofiber membrane, indicating the successful immobilization of the crown ethers onto the PVA polymer supports.

Experimental Example 3: Assay for Lithium Ion Adsorption Capacity

Adsorption experiments were carried out at 30° C. (303 K). Pre-weighed, dry CE-PVA nanofiber samples were immersed in a 10 ppm lithium solution (50 mL), and left for 48 hrs in a shaking incubator (100 rpm). Three adsorption experiments were performed for each nanofiber type. The equilibrium $Li^+$ adsorption capacities (QJ were quantitated using the following Eq. 1:

$$Q_e = \frac{(C_o - C_e) \times V}{m} \qquad (1)$$

wherein,

Co and Ce are initial and final lithium ion concentrations, respectively,

V is a sample volume, and m is a sample mass.

Figure 20:
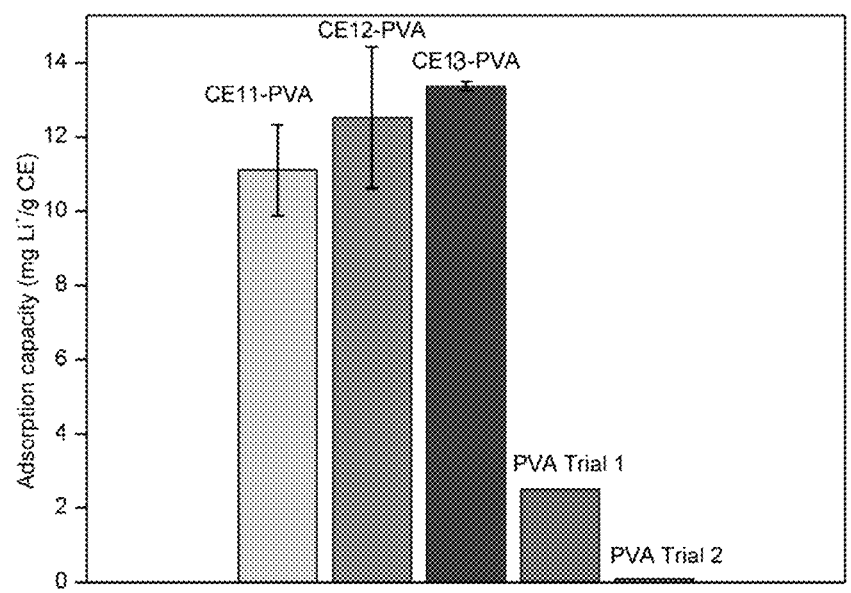
FIG. 20 is a graph showing the Li$^+$ adsorption capacities of crown ethers immobilized onto polymer nanofibers in accordance with one exemplary embodiment of the present invention.

In FIG. 20 and Table 7, the adsorption capacities of the CE-PVA nanofibers and the pure PVA nanofibers are given. As can be seen in FIG. 20 and Table 7, CE11-PVA nanofibers were measured to have a lithium adsorption capacity of 11.11 mg $Li^+$/g CE on average, while the average lithium adsorption capacities of CE12- and CE13-PVA were measured to be 12.53 and 13.38 mg $Li^+$/g CE, respectively. These values are slightly lower than the theoretical maximum adsorption capacities. The difference between the practical and theoretical maximum adsorption capacities may be attributed to the fact that the stereochemistry of crow ether, which is one of the important bases accounting for the effect of crown ether as a lithium adsorbent, is influenced by the covalent bond formed between the crown ether and the polymer support.

TABLE 7

| Crown ether | Crown ether-PVA | Theoretical maximum adsorption capacity (mgLi+/gCE) | Actual adsorption capacity (mgLi+/gCE) |
|---|---|---|---|
|  | CE 11-PVA | 20.88 | 11.11 |

TABLE 7-continued

| Crown ether | Crown ether-PVA | Theoretical maximum adsorption capacity (mgLi+/gCE) | Actual adsorption capacity (mgLi+/gCE) |
|---|---|---|---|
| (structure) | CE 12-PVA | 19.25 | 12.53 |
| (structure) | CE 13-PVA | 20.89 | 13.38 |

In FIG. 20, pure PVA nanofibers were observed to adsorb lithium ions at very low capacity, indicating that PVA is ideal as a support for crown ethers.

As described above, a lithium-selective crown ether that is synthesized through intermolecular cyclization between a bulky epoxide and a rigid aromatic compound such as 1,2-dihydroxybenzene, and which can effectively recover lithium ions is provided. The rigid aromatic group improves the rigidity of the crown ether skeleton, thus blocking preorganization effects while the bulky subunit acts to prevent complexation with large metal ions. Accordingly, the crown ether exhibits very high selectivity for lithium ions, and can effectively recover lithium ions.

For use as a lithium adsorbent, the novel crown ether with both bulky and rigid subunits is immobilized onto a polymer nanofiber. In this regard, the crown ether-immobilized polymer nanofibers may be formed into a recyclable membrane.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing a lithium-selective crown ether comprising reacting by cyclization a bis-epoxide and a hydroxy benzene,
   wherein the bis-epoxide is synthesized by reacting a diol with an allyl compound to give a dialkene compound (step a), and reacting the dialkene compound with a perbenzoic acid (step b).

2. The method of claim 1, wherein the diol is selected from the group consisting of pinacol, 2,2-diethyl-1,3-propanediol, [1,1'-bicyclopentyl]-1,1'-diol, cis-1,2-cyclohexanediol, cis-1,2-cyclopentanediol, and a combination thereof.

3. The method of claim 1, wherein the allyl compound is allyl bromide.

4. The method of claim 1, wherein the dialkene compound is selected from the group consisting of:

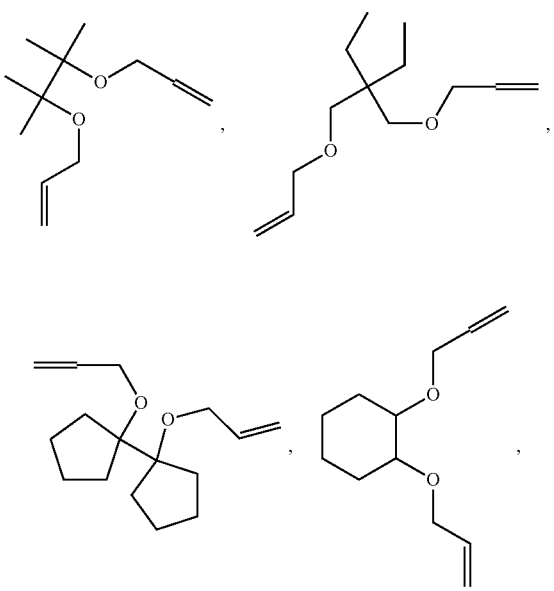

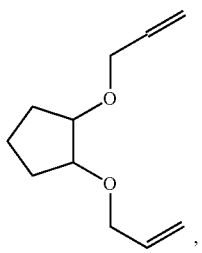

and a combination thereof.

5. The method of claim 1, wherein the perbenzoic acid is m-chloroperbenzoic acid.

6. The method of claim 1, wherein the bis-epoxide is selected from the group consisting of:

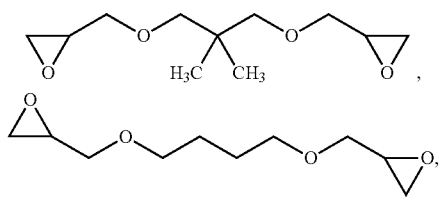

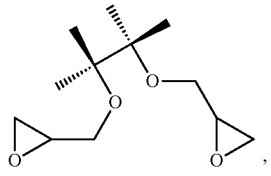

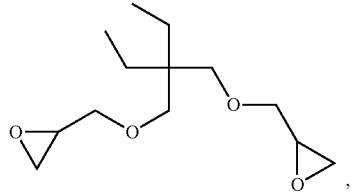

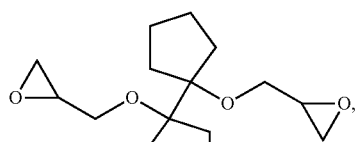

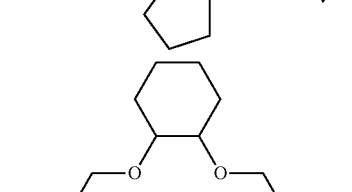

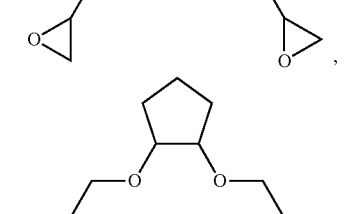

and a combination thereof.

7. The method of claim 1, wherein the hydroxybenzene is 1,2-dihydroxybenzene.

8. The method of claim 1, wherein the cyclization is carried out by reacting the bis-epoxide with the hydroxy benzene in presence of a metal hydroxide in a solvent.

9. The method of claim 1, wherein the crown ether is selected from the group consisting of:

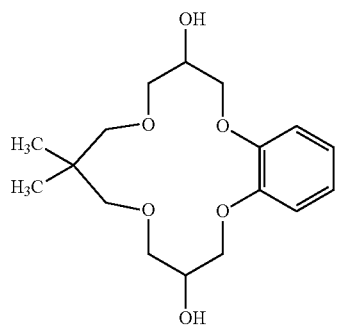

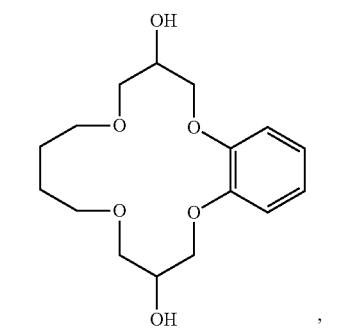

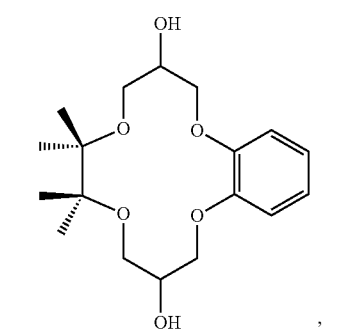

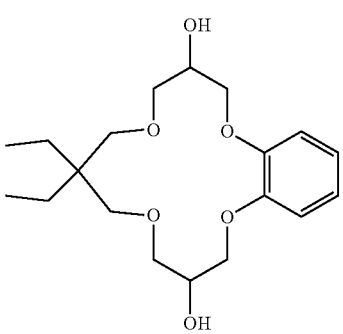

-continued

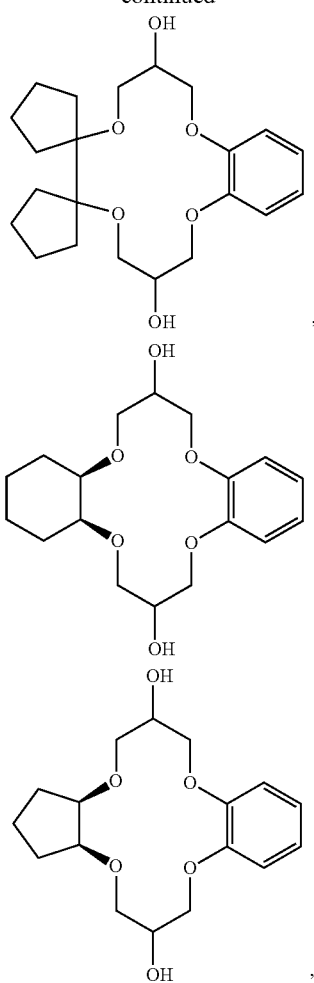

and a combination thereof.

10. A method for preparing a lithium adsorbent using a crown ether, comprising: mixing the crown ether and a polymer material in a solvent to give a dope solution (step a'); electrospinning the dope solution into polymer nanofibers (step b'); and crosslinking the nanofibers through a crosslinker to immobilize the crown ether on the polymer nanofibers (step c').

11. The method of claim 10, wherein the crown ether of step a' is selected from the group consisting of:

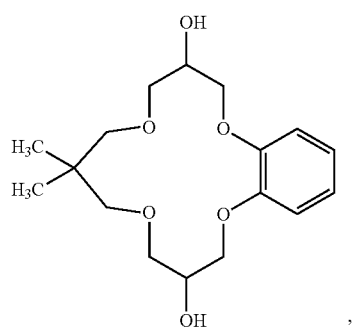

-continued

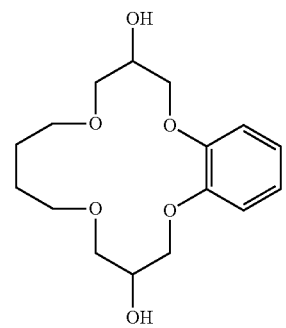 [SMILES: OC1COCCCCOCC(O)COc2ccccc2OC1]

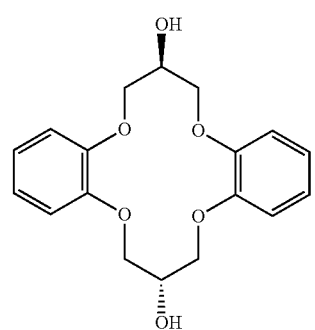

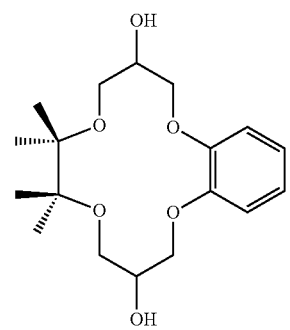

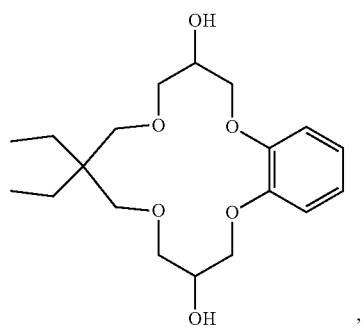

-continued

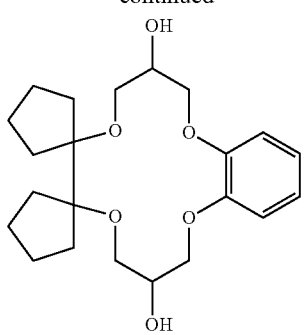

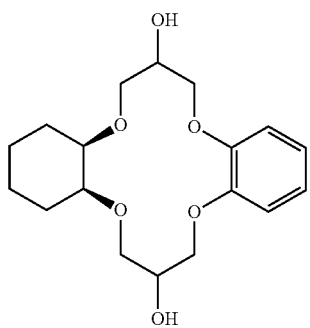

-continued

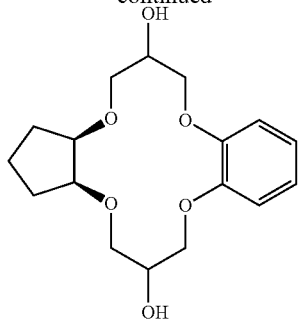

and a combination thereof.

12. The method of claim 10, wherein the polymer material is a polyvinyl alcohol.

13. The method of claim 10, wherein the crosslinking step is carried out in an aerosol manner.

14. The method of claim 10, wherein the crosslinker of step c' is glutaraldehyde.

15. The method of claim 10, wherein the crosslinker of step c' is glutaraldehyde dissolved in an acetone solution.

16. The method of claim 15, wherein the acetone solution further comprises HCl.

* * * * *